(12) United States Patent
Martin

(10) Patent No.: US 7,718,445 B2
(45) Date of Patent: *May 18, 2010

(54) METHODS AND COMPOSITIONS FOR DIRECTED MICROWAVE CHEMISTRY

(75) Inventor: Mark Martin, Rockville, MD (US)

(73) Assignee: Mirari Biosciences, Inc., Rockvillle, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/059,427

(22) Filed: Mar. 31, 2008

(65) Prior Publication Data

US 2008/0248489 A1    Oct. 9, 2008

Related U.S. Application Data

(63) Continuation of application No. 09/968,517, filed on Oct. 2, 2001, now Pat. No. 7,351,590.

(60) Provisional application No. 60/237,192, filed on Oct. 3, 2000.

(51) Int. Cl.
  *G01N 33/543*   (2006.01)
  *C12Q 1/00*     (2006.01)
(52) U.S. Cl. .............. 436/518; 436/173; 436/50; 436/51; 436/526; 436/149; 435/4; 435/6; 435/7.1; 435/287.1; 435/287.2
(58) Field of Classification Search ............ 436/518, 436/173, 806, 50, 51, 526, 149; 435/4, 6, 435/7.1, 287.1, 287.2
See application file for complete search history.

(56) References Cited

U.S. PATENT DOCUMENTS

| | | | |
|---|---|---|---|
| 3,455,842 A | 7/1969 | Cornelius et al. | |
| 3,839,175 A | 10/1974 | Keyes | |
| 4,340,672 A | 7/1982 | Kondo et al. | |
| 4,575,485 A | 3/1986 | Sizto et al. | |
| 4,745,077 A | 5/1988 | Holian et al. | |
| 4,822,492 A | 4/1989 | Chao et al. | |
| 4,822,566 A | 4/1989 | Newman | |
| 4,880,752 A | 11/1989 | Keck et al. | |
| 5,285,040 A | 2/1994 | Brandberg et al. | |

(Continued)

FOREIGN PATENT DOCUMENTS

EP        0487091        5/1992

(Continued)

OTHER PUBLICATIONS

Abati et al., "Looking forward in diagnostic pathology," Cancer, vol. 78, pp. 1-3 (1996).

(Continued)

*Primary Examiner*—Mark L Shibuya
*Assistant Examiner*—Pensee T Do
(74) *Attorney, Agent, or Firm*—Jenkins, Wilson, Taylor & Hunt, P.A.

(57) ABSTRACT

The present invention concerns a novel means by which specific chosen reactions can be accelerated through the use of a new type of artificial enzyme. The invention allows specific reactions to occur at an accelerated rate, even in the presence of other non-chosen molecules, which may be very similar in structure to the chosen reactant. The reactions may be stoichiometric or catalytic.

51 Claims, 7 Drawing Sheets

U.S. PATENT DOCUMENTS

| | | | |
|---|---|---|---|
| 5,350,686 | A | 9/1994 | Jhingan |
| 5,403,747 | A | 4/1995 | Akins et al. |
| 5,427,779 | A | 6/1995 | Elsner et al. |
| 5,451,428 | A | 9/1995 | Rupp |
| 5,478,748 | A | 12/1995 | Akins et al. |
| 5,496,701 | A | 3/1996 | Pollard-Knight |
| 5,689,008 | A | 11/1997 | Satyapae et al. |
| 5,780,578 | A | 7/1998 | Mashelkar et al. |
| 5,846,843 | A | 12/1998 | Simon |
| 5,869,349 | A | 2/1999 | Lin et al. |
| 5,911,941 | A | 6/1999 | Rokhvarger et al. |
| 5,922,537 | A | 7/1999 | Ewart et al. |
| 5,985,356 | A | 11/1999 | Schultz et al. |
| 6,011,247 | A | 1/2000 | Grillo et al. |
| 6,029,498 | A | 2/2000 | Walters et al. |
| 6,034,775 | A * | 3/2000 | McFarland et al. ............ 506/12 |
| 6,140,045 | A | 10/2000 | Wohlstadter et al. |
| 6,159,681 | A | 12/2000 | Zebala |
| 6,180,415 | B1 | 1/2001 | Schultz et al. |
| 6,235,241 | B1 | 5/2001 | Catt et al. |
| 6,255,477 | B1 | 7/2001 | Kleiber et al. |
| 6,355,491 | B1 | 3/2002 | Zhou et al. |
| 6,413,783 | B1 | 7/2002 | Wohlstadter et al. |
| 6,630,358 | B1 | 10/2003 | Wagner et al. |
| 7,348,182 | B2 * | 3/2008 | Martin et al. ............... 436/518 |
| 7,351,590 | B2 * | 4/2008 | Martin ...................... 436/518 |

FOREIGN PATENT DOCUMENTS

| | | |
|---|---|---|
| GB | 1363526 | 8/1974 |
| JP | S64-002608 | 1/1989 |
| JP | H03-238895 | 10/1991 |
| JP | H04-260472 | 9/1992 |
| JP | H06-043161 | 2/1994 |
| JP | H08-105892 | 4/1996 |
| JP | H09-255365 | 9/1997 |
| JP | H09-297138 | 11/1997 |
| WO | WO02/29076 | 4/2002 |

OTHER PUBLICATIONS

Baziard et al., "Cross-linking under microwaves (2.45 GHz) of aluminum powder-epoxy resin composites I. Electrical power dependence," European Polymer Journal, vol. 24, p. 873 (1988).

Bekkum et al., "Supported Zeolite Systems and Applications," Studies in Surface Science and Catalysis, Elsevier Science B.V., Amsterdam, NI, vol. 85, pp. 509-542 (1994).

Boon et al., "Microwave Cookbook of Pathology," Coulomb Press, Leiden. vol. 17, pp. 1-219 (1989).

Borchart et al., "Synthetic receptor binding elucidated with an encoded combinatatorial library," Journal of American Chemical Society, vol. 116, p. 373 (1994).

Borman, "Combinatorial Chemistry," Chemical and Engineering News, pp. 49-58 (Aug. 21, 2001).

Bose et al., "MORE Chemistry in Microwave," Chemtech, vol. 27, No. 9, pp. 18-25 (1997).

Bowie et al., "Analytical applications of liquid phase chemiluminescence reactions—a review," Journal of Bioluminescence and Chemiluminescence, vol. 11, pp. 61-90 (1996).

Bram et al., "Alkylation of Potassium Acetate in 'Dry Media' Thermal Activation in Commercial Microwave Ovens," Tetrahedron, vol. 46, p. 5167 (1990).

Bram et al., "Anthraquinone Microwave-Induced Synthesis in Dry Media in Domestic Ovens," Chem. Ind., p. 396 (1991).

Breslow et al., "Optimization of metallocene substrates for beta-cyclodextrin reactions," Journal of American Chemical Society, vol. 105, p. 2739 (1983).

Buffler et al., "Microwave processing of materials," Materials Research Society Symposium Proceedings, vol. 430, p. 85 (1996).

Burow et al., "Molecular imprinting: Synthesis of polymer particles with antibody-like binding characteristics for glucose oxidase," Biochemical and Biophysical Research Communications, vol. 227, p. 419 (1996).

Bystrom et al., "Selective reduction of steroid 3- and 17-ketones using LiAlH4 activated template polymers," Journal of the American Chemical Society, vol. 115, p. 2081 (1993).

Cooper, "Applications of microarray technology in breast cancer research," Breast Cancer Research, vol. 3, pp. 158-175 (2001).

Cornelis et al., "Oxidation of Alcohols by Clay-Supported Iron (III) Nitrate; A New Efficient Oxidizing Agent," Synthesis, vol. 1980, pp. 849-850 (Oct. 1980).

Dai et al., "Imprint Coating: a novel synthesis of selective functionalized ordered mesoporous sorbents," Angewandte Chemie International Edition, vol. 38, p. 1235 (1999).

Dickert et al., "Molecularly imprinted polymers for optichemical sensors," Advanced Materials, vol. 8, p. 987 (1996).

Dolle et al., "Comprehensive survey of combinatorial library synthesis: 1999," Journal of Combinatorial Chemistry, vol. 2, pp. 383-433 (2000).

Draghici et al., "Experimental design, analysis of variance and slide quality assessment in gene expression arrays," Current Opinion in Drug Discovery and Development, vol. 4, pp. 332-337 (2001).

Fodor et al., "Multiplexed Biochemical Assays with Biological Chips," Nature, vol. 3, pp. 555-556 (1993).

Folkman, "Angiogenesis and angiogenesis inhibition: an overview," EXS, vol. 79, pp. 1-8 (1997).

Freeman et al., "Quantitative RT-PCR: Pitfalls and potential," BioTechniques, vol. 26, pp. 112-125 (1985).

Gabriel et al., "Dielectric Parameters Relevant to Microwave Dielectric Heating," Chemical Society Reviews, vol. 27, pp. 213-224 (1998).

Gallop et al., "Applications of Combinatorial Technologies to Drug Discovery. 1. Background and Peptide Combinatorial Libraries," Journal of Medicinal Chemistry, vol. 37, No. 9, pp. 1233-1251 (1994).

Glad et al., "Use of Silane monomers for molecular imprinting and enzyme entrapment in polysiloxane-coated porous silica," Journal of Chromatography, vol. 347, p. 11 (1985).

Gordon et al., "Applications of Combinatorial Technologies to Drug Discovery. 2. Combinatorial Organic Synthesis, Library Screening Strategies and Future Directions," Journal of Medicinal Chemistry, vol. 37, No. 10, pp. 385-401 (1994).

Gu et al., "Photo-fries reactions of 1-Naphthyl esters in cation-exchanged zeolite Y and Polyethylene media," Journal of American Chemical Society, vol. 121, p. 9467 (1999).

Harkin, "Uncovering functionally relevant signaling pathways using microarray-based expression profiling," Oncologist, vol. 5, pp. 501-507 (2000).

Hasted, "Aqueous dielectrics," Chapman & Hall, London, pp. 1-255 (1973).

Hergenrother et al., "Small-Molecule Microarrays: Covalent Attachment and Screening of Alcohol-Containing Small Molecules on Glass Slides," Journal of American Chemical Society, vol. 122, pp. 7849-7850 (2000).

Hilpert et al., "Anti-c-myc Antibody 9E10: Epitope Key Positions and Variability Characterized Using Peptide Spot Synthesis on Cellulose," Protein Engineering, vol. 14, pp. 803-806 (2001).

Holzworth et al., "Enhanced microwave heating of nonpolar solvents by dispersed magnetic nanoparticles," Industrial and Engineering Chemistry Research, vol. 37, p. 2701 (1998).

Huhmer et al., "Noncontact infrared-mediated thermocycling for effective polymerase chain reaction amplification of DNA in Nanoliter volumes," Analytical Chemistry, vol. 72, pp. 5507-5512 (2000).

Jacobs et al., "Combinatorial Chemistry—Applications of Light-Directed Chemical Synthesis," Trends in Biotechnology, vol. 12, pp. 19-26 (1994).

Jansen et al., "Preparation of Coatings of Molecular Sieve Crystals for Catalysis and Separation," Studies in Surface Science and Catalysis, Elsevier Science B.V., Amsterdam, NI, vol. 85, pp. 215-250 (1994).

Jansen et al., "Advanced zeolite science and applications," Jansen et al. eds., Elsevier, New York, pp. 215-250 (1994).

Jiang et al., "Template-directed preparation of macroporous polymers with oriented and crystalline arrays of voids," Journal of American Chemical Society, vol. 121, p. 11630 (1999).

Jin et al., "Application of microwave techniques in analytical chemistry," Trends in Analytical chemistry, vol. 18, pp. 479-484 (1999).

Johnson, "All's Well that Ends Well: a Profile of Specialty Microwell Plates," The Scientist, vol. 13, p. 16 (1999).

Jones, "Membrane immobilization of nucleic acids: Part 1: Substrates," IVD Technology, vol. 7, No. 6, pp. 50-54 (2001).

Kappe, "High-Speed Combinatorial Synthesis Utilizing Microwave Irradiation," Current Opinion in Chemical Biology, vol. 6, pp. 314-320 (2002).

Kappe, "Speeding up Solid-Phase Chemistry by Microwave Irradiation: a Tool for High-Throughput Synthesis," American Laboratory, vol. 23, pp. 13-19 (2001).

Kempe et al, "An approach towards surface imprinting using the enzyme ribonuclease A," Journal of Molecular Recognition, vol. 8, p. 35 (1995).

Kidwai et al., "A novel enzymatic synthesis of 2-substituted Naphtho[2,1-b]-pyran-3-ones using microwaves," Indian Journal of Chemistry Section B: Organic Chemistry including Medicinal Chemistry, vol. 37B, p. 963 (1998).

Korbel et al., "Reaction Microarrays: a Method for Rapidly Determining the Enantiomeric Excess of Thousands of Samples," Journal of American Chemical Society, vol. 123, pp. 361-362 (2001).

Kramer et al., "Synthesis and Screening of Peptide Libraries on Continuous Cellulose Membrane Supports," Methods in Molecular Biology, vol. 87, pp. 25-39 (1998).

Kricka, et al., "Nucleic acid detection technologies—labels strategies, and formats," Clinical Chemistry, vol. 45, pp. 453-458 (1999).

Krishnan et al., "Solid-phase extraction techniques for the analysis of biological samples," Journal of Pharmaceutical and Biomedical Analysis, vol. 12, pp. 287-294 (1994).

Kubrakova, I.V., "Effect of microwave radiation on physiochemical process in solutions and heterogeneous systems: applications in analytical chemistry," Journal of Analytical Chemistry, vol. 55, pp. 1113-1122 (2000).

Laszlo, T.S., "Industrial applications of microwaves," The Physics Teacher, pp. 570-579 (Nov. 1980).

Leitzel et al., "Detection of cancer cells in peripheral blood of breast cancer patients using reverse transcription-polymerase chain reaction for epidermal growth factor receptor," Clinical Cancer Research, vol. 4, pp. 3037-3043 (1998).

Lennon, G.G., "High-throughput gene expression analysis for drug discovery," Drug Discovery Today, vol. 5, pp. 59-66 (2000).

Leonhardt et al., "Enzyme-mimicking polymers exhibiting specific substrate binding and catalytic functions," Reactive Polymers, vol. 6, p. 285 (1987).

Lew et al., "Increasing rates of reaction: microwave-assisted organic synthesis for combinatorial chemistry," Journal of Combinatorial Chemistry, vol. 4, pp. 95-105 (2002).

Lidstrom et al., "Enhancement of combinatorial chemistry by microwave-assisted organic synthesis," Combinatorial Chemistry and High Throughput Screening, vol. 5, pp. 441-458 (2002).

Lidstrom et al., "Microwave-assisted organic synthesis—a review," Tetrahedron, vol. 57, pp. 9225-9283 (2001).

MacBeath et al., "Printing small molecules as microarrays and detecting protein—ligand interactions en Masse," Journal of American Chemical Society, vol. 121, pp. 7967-7968 (1999).

Makote et al., "Dopamine recognition in templated silicate films," Chemical Communications, vol. 3, p. 425 (1998).

Marx, J., "DNA arrays reveal cancer in its many forms," Science, vol. 289, pp. 1670-1672 (2000).

Mathew-Krotz et al., "Imprinted polymer membranes for the selective transport of targeted neutral molecules," Journal of American Chemical Society, vol. 118, p. 8134 (1995).

Maugh, T. H., "Semisynthetic enzymes are new catalysts," Science, vol. 222, pp. 151-153 (1984).

Maugh, T.H., "Catalysts that break nature's monopoly," Science, vol. 221, pp. 351-354 (1983).

Maugh, T.H., "Need a catalyst? Design an enzyme," Science, vol. 223, pp. 269-271 (1983).

Mingos et al., "Applications of microwave dielectric heating effects to synthetic problems in chemistry," Chemical Society Reviews, vol. 20, pp. 1-47 (1991).

Mokaya, R., "Ultrastable mesoporous aluminosilicates by grafting routes," Angewandte Chemie International Edition, vol. 38, p. 2930 (1999).

Narrlow et al., "Acrylic polymer preparations containing recognition sites obtained by imprinting with substrates," Journal of Chromatography, vol. 229, p. 29 (1984).

Nesatyy et al., "Microwave-assisted protein staining: mass spectrometry compatible methods for rapid protein visualization," Rapid Communications in Mass Spectrometry, vol. 16, pp. 272-280 (2002).

Notice of Allowance corresponding to U.S. Patent No. 7,351,590 dated Jan. 16, 2008.

Notice of Allowance corresponding to U.S. Patent No. 7,348,182 dated Jan. 16, 2008.

O'Shannessy et al., "Molecular imprinting of amino acid derivatives at low temperature (0° C) using photolytic homolysis of azobisnitriles," Analytical Biochemistry, vol. 177, p. 144 (1989).

O'Shannessy et al., "Recent advances in the preparation and use of molecularly imprinted polymers for enantiomeric resolution of amino acid derivatives," Journal of Chromatography, vol. 470, p. 391 (1989).

Office Action corresponding to U.S. Patent No. 7,351,590 dated Jan. 9, 2006.

Official Action corresponding to an Australian Patent Application No. 2003254187 dated Jun. 2, 2008.

Office Action corresponding to U.S. Patent No. 7,351,590 dated Apr. 5, 2005.

Office Action corresponding to U.S. Patent No. 7,351,590 dated Nov. 3, 2006.

Office Action corresponding to U.S. Patent No. 7,348,182 dated Nov. 9, 2006.

Office Action corresponding to U.S. Patent No. 7,348,182 dated Oct. 19, 2005.

Office Action corresponding to U.S. Appl. No. 10/842,512 dated Jan. 24, 2008.

Office Action corresponding to U.S. Appl. No. 10/842,512 dated Jan. 8, 2007.

Office Action corresponding to U.S. Appl. No. 10/842,512 dated Oct. 19, 2005.

Office Action corresponding to U.S. Appl. No. 11/105,460 dated Jan. 14, 2008.

Office Communication corresponding to the European Patent Application No. 01979344.7-2404 dated Feb. 15, 2007.

Official Action corresponding to Japanese Patent Application No. 2002-532645 dated Mar. 25, 2008.

Olmedo et al., "Microwave absorbing materials based on conducting polymers," Advanced Materials, vol. 5, p. 373 (1993).

Pasinetti, G.M., "Use of cDNA microarray in the search for molecular markers in the onset of Alzheimer's disease dementia," Journal of Neuroscience Research, vol. 65, pp. 471-476 (2001).

Robinson, J.K., "New Molecular Beacon Technology," American Laboratory, vol. 28, p. 34. (Dec. 2000).

Roda et al., "Bio- and Chemiluminescence in Bioanalysis," Fresenius Journal of Analytical Chemistry, vol. 3, pp. 752-759 (2000).

Rouhi, A.M., "Boxed in: chemistry in confined spaces," Chemical and Engineering News, pp. 40-47 (Aug. 27, 2001).

Roussy et al. "Foundations and industrial applications of microwave and radio frequency fields," John Wiley & Sons, NY., pp. 445-466 (1995).

Schena et al., "Quantitative monitoring of gene expression patterns with a complementary DNA microarray," Science, vol. 270, pp. 467-470 (1995).

Schmalzing et al., "Capillary electrophoresis-based immunoassays," Electrophoresis, vol. 21, pp. 3919-3930 (2000).

Seiden et al. "PCR- and RE-PCR-based methods of tumor detection: potential applications and clinical implications," Important advances Oncol. Lippincott-Raven, Philadelphia, PA. pp. 191-204 (1996).

Shi et al., "Template-imprinted nanostructured surfaces for protein recognition," Nature, vol. 398, pp. 593-597 (1999).

Sidransky, D., "Nucleid acid-based methods for the detection of cancer," Science, vol. 278, pp. 1054-1058 (1997).

Slyadnev et al., "Photothermal temperature control of a chemical reaction on a microchip using an infrared diode laser," Analytical Chemistry, vol. 73, pp. 4037-4044 (2001).

Stein et al. "Microwave processing of materials," Committee on microwave Processing of Materials; National Materials Advisory Board; Commission on Engineering and Technical Systems; and National Research Council; Microwave processing of Materials, Washington, DC, National Academy Press (1994).

Varma, R. "Microwave Accelerated Solvent-Free Chemical Reactions," AMPERE Newsletter, Issue 29, ISSN 1361-8598; pp. 3-4 (2001).

Wathey et al., "The impact of microwave-assisted organic chemistry on drug discovery," Drug Discovery Today, vol. 7, pp. 373-380 (2002).

Wood, W.G., "Luminescence immunoassays: problems and possibilities," Journal of Clinical Chemistry and Clinical Biochemistry, vol. 22, pp. 905-918 (1984).

www.novacap.com, Novacap Technical Bulletin (undated).

Yang et al., "Heirarchically ordered oxides," Science, vol. 282, p. 2244 (1998).

Yu et al., "Enhanced coupling efficiency in solid-phase peptide synthesis by microwave irradiation," Journal of Organic Chemistry, vol. 57, pp. 4781-4784 (1992).

Zlotorzynski, A., "The application of microwave radiation to analytical and environmental chemistry," Critical Reviews in Analytical Chemistry, vol. 25, p. 43 (1995).

Zubritsky, E., "Spotting a microarray system," Modern Drug Discovery, pp. 59-71 (May 2001).

Official Action corresponding to Japanese Patent Application No. 2004-534253 dated Oct. 7, 2008.

Communication Pursuant to Article 94(3) EPC corresponding to European Patent Application No. 01 979 344.7-2404 dated Feb. 17, 2009.

Office Communication corresponding to U.S. Appl. No. 10/842,512 dated Oct. 14, 2009.

Issued Patent corresponding to Australian Patent Application No. 2003254187 dated Oct. 29, 2009.

* cited by examiner

1. Dielectric Core
2. Specific Reagent Binding Sites
3. (Optional) Porous Coat a)

Liquid medium

1. Dielectric Surface
2. Specific Reagent Binding Sites
3. (Optional) Porous Coat b)

1. capture membrane

2. Underlying support (inert)
3. spotted dielectric array c)

1. capture membrane

2. Underlying support (inert)
3. layered dielectric

METHODS AND COMPOSITIONS FOR DIRECTED MICROWAVE CHEMISTRY

CROSS-REFERENCE TO RELATED APPLICATIONS

This application is a continuation of U.S. patent application Ser. No. 09/968,517, filed Oct. 2, 2001 now U.S. Pat. No. 7,351,590, which is a continuation-in-part of U.S. Provisional Patent Application Ser. No. 60/237,192 filed on Oct. 3, 2000, the contents of each of which are herein incorporated by reference in their entirety.

FIELD OF THE INVENTION

The present invention relates to the field of artificial enzymes and artificial protein receptors. It also relates to the field of microwave chemistry.

BACKGROUND OF THE INVENTION

Until now, no one has ever combined the field of artificial enzymes/antibodies with the field of dielectric chemistry. The state of the art in these two separate areas (microwave chemistry and artificial enzymes/receptors) is described as follows.

Microwave Chemistry

Microwaves (including radiofrequency or RF electromagnetic radiation) are commonly used in wireless communication devices. Advances in microwave transmission have improved along with tremendous recent technological improvements in the satellite and communications industry (for example, in cell phones and wireless internet).

Microwaves are also well known in common kitchen appliances. Microwave ovens heat water-containing food rapidly because water is efficient at converting microwave energy to thermal energy. Kitchen microwave ovens emit microwaves at a frequency of 2.45 GHz, which is well within the microwave absorption spectrum of water. Frequencies outside of the absorption spectrum of water would not heat food as well.

Another use for microwaves is in chemical reaction applications (Bose et al., 1997; Bradley, 2001). Microwave chemistry refers to the use of microwaves to accelerate chemical reactions. Reactions are usually carried out using microwave radiation to heat bulk solutions that contain the reactants (Mingos & Baghurst, 1991; Zlotorzynski, 1995). Often these reactions are carried out in non-aqueous solvents. Microwave ovens specifically designed for use in carrying out microwave chemistry of bulk reaction solutions are commercially available (CEM Corporation (Mathews, N.C.), Milestone, Inc. (Monroe, Conn.), Personal Chemistry AB (Uppsala, Sweden)).

Microwave accelerated reactions are sometimes run on solvent-free supports such as alumina and silica (Varma, 2001; Bose, 1997). The supports can be doped with reagents, for example in detoxifying waste. The supports are chosen because they are inexpensive and recyclable agents which non-specifically adsorb/extract the reagent of interest. No specific binding of (such as by antibodies) is used to capture reagents.

Microwave-enhanced catalysis has also been described (Roussy & Pearce, 1995). The term "microwave-enhanced catalysis" has been used to refer to conventional catalysis, rather than to catalysis that occurs in enzyme-like binding pockets in aqueous solution. One example of such usage of the term "microwave-enhanced catalysis" is the isomerization of liquid hexane using a metallic $Pt/Al_2O_3$ catalyst. Another example is the partial oxidation of gaseous methane using a catalyst that is an oxide of $SmLiO_2$ doped with CaO and MgO (Roussy & Pearce, 1995).

Another example of the application of microwaves to accelerate chemical reactions is the use of microwave-absorbing particles to enhance the heating of a bulk solution (Holzwarth et al., 1998). In this case, dispersed cobalt and magnetite nanoparticles were used as microwave (2.45 GHz) absorbers to heat a bulk xylene solution. Xylene is a non-polar solvent not appreciably heated by microwaves at 2.45 GHz. In one such case, microwaves were used to accelerate the rate of an enzyme-catalyzed reaction (Kidwai et al., 1998). However, here the microwaves were not directed, but used to heat the bulk solution.

In another application, microwaves have been used to heat the bulk solvent during solid-phase combinatorial chemistry (Kappe, 2001; Bradley, 2001). In these cases, conventional resins (polystyrene, for example) as solid scaffolds for chemistry. The bulk solution was the target of the microwave heating.

In another case, microwaves were used to accelerate a chromogenic reaction between noble metals and chromogenic reagents. This analytical reaction was performed in solution by flow injection analysis (FIA) (Jin et al., 1999). The reaction depended on bulk solvent heating rather than targeted dielectric material heating.

In yet another case, microwaves were used to enhance the solution phase formation of a fluorescent complex of aluminum (Kubrakova, 2000). The fluorescence intensity could be used to measure aluminum ions in solution. Again, the reaction depended on bulk heating of solvent.

Artificial Enzymes/Receptors

Nature uses specifically folded proteins called enzymes to catalyze specific reactions necessary for the function of a living organism. Nature also uses non-catalytic proteins, such as receptors and antibodies to effect other biological processes. Both catalytic and non-catalytic proteins have remarkable pockets on their surfaces that bind to the appropriate molecule with exquisite specificity. In the case of enzymes, when the appropriate molecule is bound in the binding pocket (called an "active site"), a chemical reaction takes place that converts the molecule (substrate) into a chemically different molecule (product). The reaction product dissociates form the active site, allowing the (unaltered) enzyme to bind and catalyze another reaction "turnover".

Protein-based enzymes, receptors, and antibodies are often used in industry, medicine, and diagnostics as reagents. For example, antibodies are used as therapeutic agents for various diseases including cancer and rheumatoid arthritis. Enzymes are used to "fade" denim blue jeans and to process high fructose corn syrup. Antibodies and enzymes are used in immunoassays in medical diagnostics. Despite the widespread use of naturally occurring antibodies and enzymes, many laboratories have sought to create artificial antibodies, receptors, and enzymes. One drawback of the use of natural proteins, or modified natural proteins, for practical purposes, is that proteins are not particularly stable molecules. Artificial reagents would have greater stability to non-physiological temperatures, pH values, non-aqueous solvents, and salt concentrations. Also, natural proteins are susceptible to degradation by contaminating enzymes called proteases that hydrolytically cleave and inactivate other proteins. In addition, even under ideal storage conditions (cold storage in a suitable buffer) the shelf life of proteins can be very short. Finally, in many cases a binding or catalytic reagent is desired for which there is no known natural antibody or enzyme. For example, an antibody may be desired that binds a very small molecule such as methanol or an enzyme may be desired that carries out a chosen stereospecific reaction during preparation of a fine chemical.

Because of the above-stated drawbacks of natural proteins, many laboratories have developed non-protein bio-mimetic compounds that function in the same way as antibodies or enzymes. A wide range of classes of chemical structures has been shown to be useful as artificial proteins. In all cases, the artificial biomolecules have binding pockets that specifically bind to a molecule of choice. These include, but are not limited to; molecularly imprinted polymers (Dai, et al., 1999; Dickert & Thierer, 1996; Leonhardt & Mosbach, 1987), chiral ligands (Maugh 1983a), cavitands (Maugh 1983b, Breslow et al., 1983) and zeolites, and other low molecular weight organic synthetic receptors (Borchart & Clark, 1994). In addition, natural proteins are often sought out or modified to have enhanced stability (thermal or other) (Maugh, 1983c).

Individuals who have made artificial enzymes or antibodies/receptors have never reported the possibility that directed microwave energy could be used to promote the rate of a chemical reaction within the binding site of the biomimetic.

The present invention combines salient features of these two previously unassociated fields. By combining certain aspects of these fields it has been discovered that the rate of chemical reactions can be accelerated by the energy of microwave radiation and with the exquisite regio- and stereo-specificity of natural enzymes.

The present invention reveals a novel means of using microwave energy to specifically accelerate chosen chemical reactions. The reaction specificity comes from the fact that the microwaves are directed to lossy (see definitions below) materials that contain specific binding sites for the desired reactant. The invention describes new uses of microwave radiation. It has never before been disclosed how to direct dielectric heat to accelerate the reaction of a specific molecule in a mixture of similar and/or dissimilar molecules. In this way, the invention describes a new form of artificial enzyme. The results are obtained by using a dielectric material that has substantially better heating properties than water at the chosen microwave emission frequency. A specific reactant-binding molecule is in association with the preferentially heated dielectric material, causing the enhanced reaction of bound reactant.

OBJECTS OF THE INVENTION

The invention is directed toward an improved means for accelerating the rate of specific chemical reactions. A further objective of the invention is to confer tailored enzyme-like regio- and stereo-specificity to a reaction. A still further objective of the invention is to provide such improved reaction rates and specificity to a diverse number and type of chemical reactions. It is yet another objective of the invention that the accelerated reactions be controllable, so that they can be turned on or off, or be modulated, by a user at will. It is yet another objective of this invention to allow specific reactions to be accelerated regardless of whether the reaction is in a homogeneous or heterogeneous solution or suspension, or is bound or otherwise associated with a solid support (such as a surface, bead, etc.). It is yet another objective of the invention to provide a method for accelerating a chosen reaction in the presence of other compounds that may be very similar in structure to the desired reactant, but will not appreciably react.

a) The surface can be a permanent dielectric within the microwave oven or it could be a disposable device such as a cartridge or cassette. The diagram shows what is enclosed in a microwave oven chamber during a reaction. In some applications, the planar surface can be removed from solvent prior to microwave irradiation.

b) Chip for directed microwave chemistry. In this case, the surface (chip or other essentially planar object) comprises a support (e.g. glass or Teflon), spotted dielectric, and a membrane or other reagent capture surface.

c) Chip for directed microwave chemistry. Similar to b) except the dielectric is in the form of a layer rather than spots.

Figure 3:
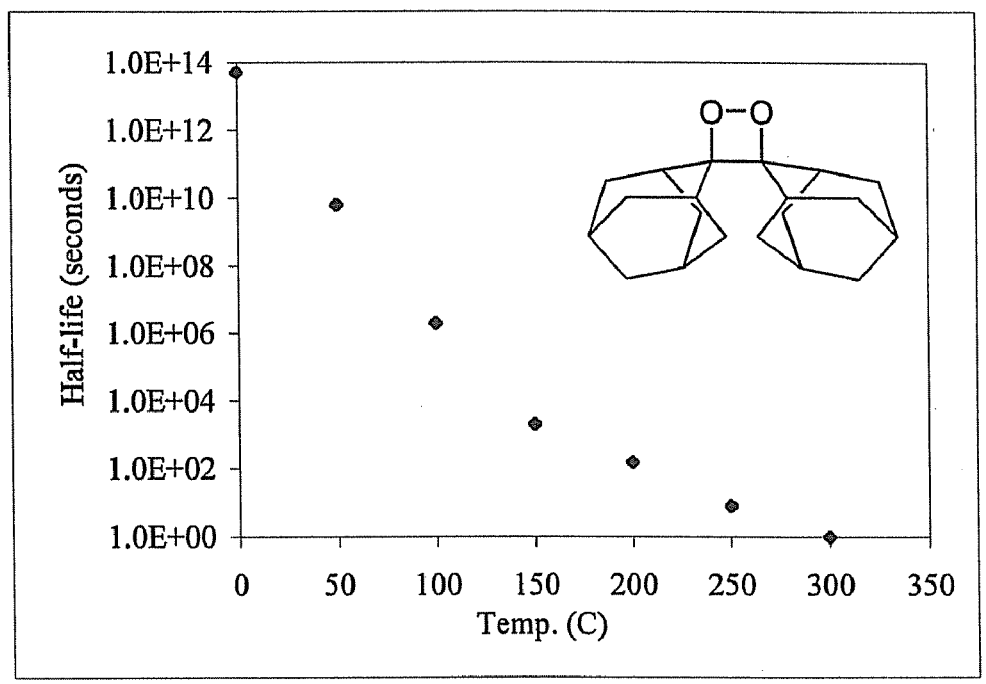

FIG. 3: Half-life of Adamantylidene adamantine 1,2-dioxetane versus temperature. The figure illustrates the strong dependence of the dioxetane half-life on temperature (dioxetane breakdown initiates CL). Note that the abscissa scale is logarithmic.

Figure 4:
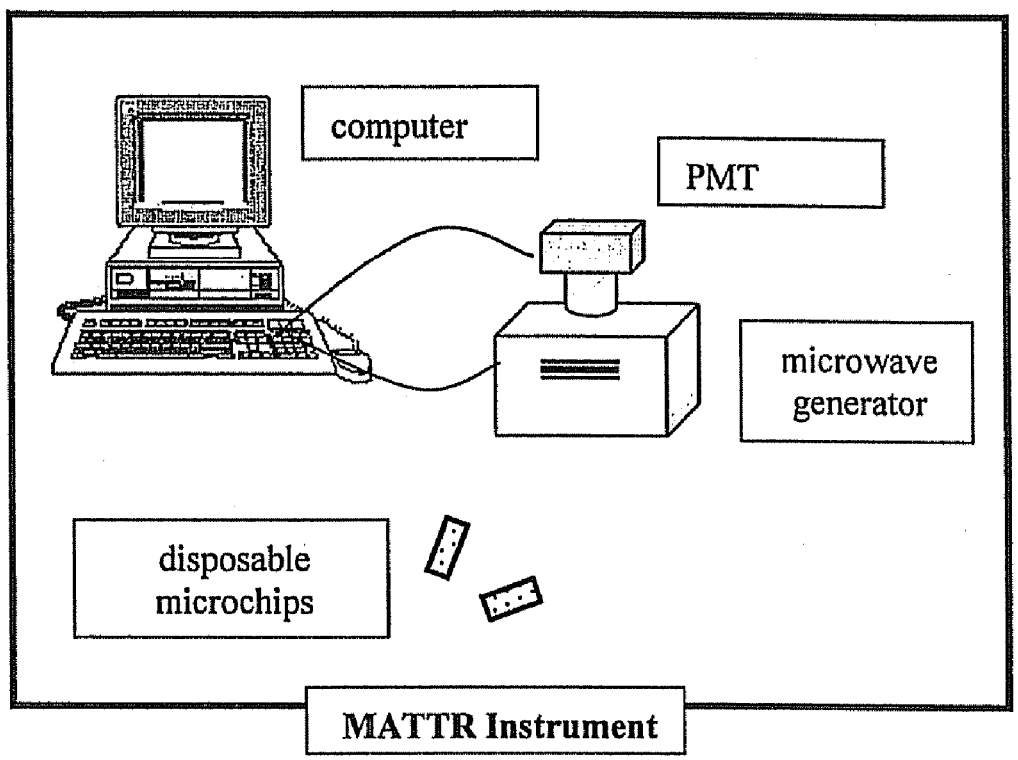

FIG. 4: A MATTR instrument. The components of the instrument are a microwave oven with a built-in holder for MATTR disposable chips. The chips emit light upon microwave heating, which is captured by a PMT (either directly through a window or via fiber optics). Microwave generation, camera recording, and image analysis are all carried out using a PC.

Figure 5:
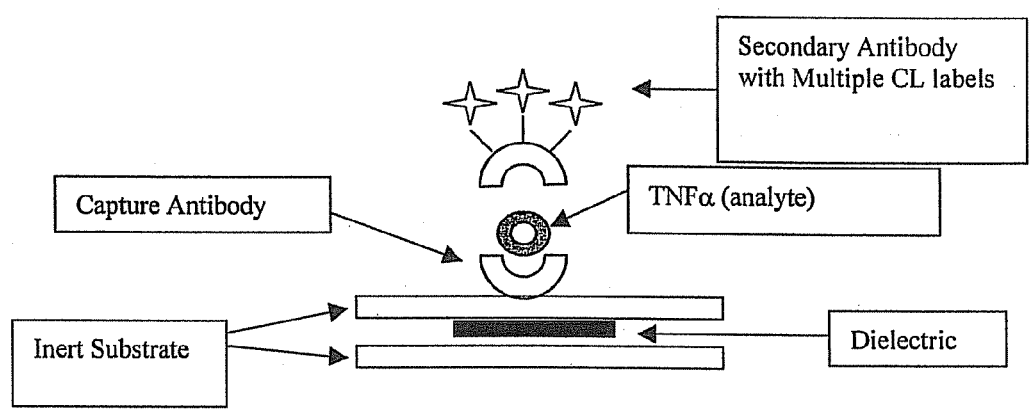

FIG. 5: MATTR-based sandwich immunoassay TNFα immunoassay. Upon microwave heating, light emission from multiple CL labels will signal the presence of the analyte, TNFα.

Figure 6:
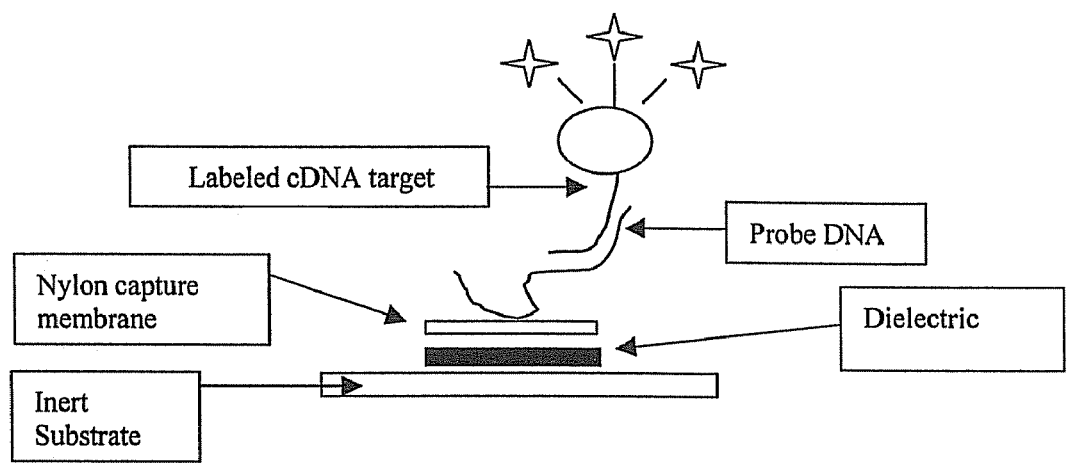

FIG. 6: MATTR-based nucleic acid microarray assay. Upon microwave heating, light emission from multiple CL labels signals the presence of the analyte.

Figure 7:
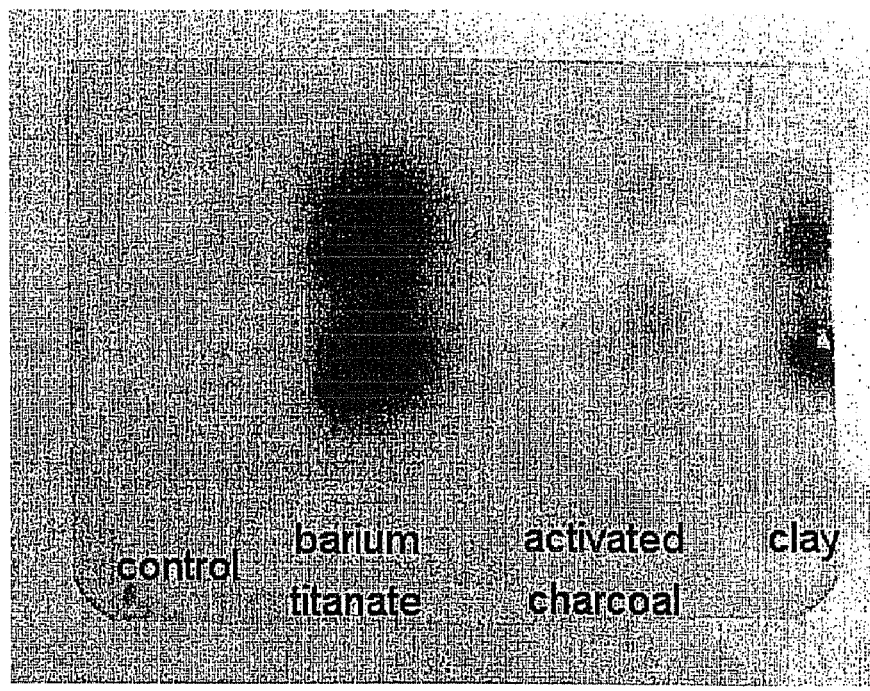

FIG. 7: Demonstration of Microwave-Accelerated Triggered Chemiluminescent Reactions. This figure demonstrates that, compared with "blank" glass microscope slide-based chips, dielectric chips containing barium titanate, activated carbon, or Bentonite clay substantially accelerate the chemiluminescent reaction of luminol/peroxide under microwave irradiation.

SUMMARY OF THE INVENTION

The invention describes a means in which chemical reactions (catalytic or stoichiometric) can be accelerated and be given exquisite enzyme-like specificity. The reactions preferably occur on solid phases or surfaces (hereinafter collectively referred to as "solid supports"). Suitable solid supports preferably contain: a dielectric (microwave absorbing) material, a specific binding reagent (such as an artificial antibody or artificial enzyme, etc.), and optionally a thermally-insulating porous coating that is permeable to the reagent. The solid support can be in many forms, most notably beads and planar surfaces. The solid supports are preferably bathed in aqueous or organic solution containing the chosen reagent. Next, depending on the application, the solid supports are preferably either left in the solvent or are removed, for example, into air, etc. Microwaves are then emitted into the solid surface. In cases where the solid support is left in solvent, the microwaves are emitted at a frequency that heats the dielectric more than the solvent. The instrument power, frequency, and duration of the microwave emission are pre-determined in the laboratory. Following microwave heating, a change in the reagent may be noted by some physico-chemical change that takes place in the formation of product(s) from reactant(s). The specific chemical rate acceleration can be used for preparative and analytical applications. In analytical applications, the reaction may be monitored and may be quantitated, for example in medical diagnostics, by an accompanied observable physico-chemical change (color change, for example).

In accordance with the principles of the present invention, the reaction on a solid support coated with or otherwise containing an artificial enzyme may be accelerated by: (1) adjusting the concentration of the reactant by binding to a large number of specific binding sites on the solid support, or (2) adjusting the temperature difference between the dielectric/artificial enzyme and the bulk solution.

In detail, the invention provides a method for accelerating a chemical reaction of a reactant specifically bound to a surface, the method comprising;
 (a) contacting a composite with the reactant, the composite comprising a solid material susceptible to dielectric heating and a specific binding molecule for the reactant,
 (b) applying an electromagnetic field to the composite, resulting in dielectric heating of the solid material, and
 (c) allowing the heated reactant to react, thereby accelerating the reaction.

The invention additionally concerns a method for accelerating a chemical reaction of a reactant specifically bound to a surface, the method comprising;
 (a) contacting a composite, the composite comprising a solid material susceptible to dielectric heating and a specific binding molecule for the reactant, with a reactant-containing solution for a time sufficient to allow reactant to bind to composite,
 (b) separating the composite-reactant complex from the solution,
 (c) applying an electromagnetic field to the composite, resulting in dielectric heating of the solid material, and
 (d) allowing the reactant to be converted to product, thereby accelerating the reaction.

The invention additionally concerns the embodiments of such methods further comprising the step of measuring the extent of reaction, and controlling the application of the electromagnetic field in response to the measured extent of reaction and/or wherein the step of contacting comprises mixing the composite into a solution containing the reactant and/or wherein the step of contacting comprises mixing the reactant into a liquid containing the composite.

The invention additionally concerns the embodiments of such methods wherein the wavelength of the applied field is between 5 cm and 100 m, and wherein the chemical reaction is hydrolysis, homolytic cleavage, or a chemiluminescent reaction.

The invention additionally concerns the embodiments of such methods:
 1. wherein the solid material is selected from the group consisting of carbon, charcoal, amorphous carbon, carbon black, clay, and nickel;
 2. wherein the solid material is an oxide selected from the group consisting of copper oxide, chromium oxide, silicon oxide, niobate oxide and manganese oxide
 3. wherein the solid material is a titanate selected from the group consisting of barium titanate, and an inorganic titanate;
 4. wherein the solid material is an alumina compound selected from the group consisting of alumina-magnetite, aluminum-epoxy composite and calcium aluminate;
 5. wherein the solid material is an oxide or non-oxide ceramic, a ferrite, a ferroelectric polymer, or an organic polymer; and/or
 6. wherein the solid material is selected from the group consisting of SiC, Si, Mg, FeSi, $Cr_2O_3$, $Fe_3O_4$, $MnO_2$, NiO.

The invention additionally concerns the embodiments of such methods wherein the solid material is a mixture of a conductive material and an insulator, and especially wherein the conducting powder is Nb, TaC, SiC, $MoSi_2$, Cu, or Fe, and the insulator is $ZrO_2$, $Y_2O_3$, or $Al_2O_3$. The conductive materials may be metals, and may be granular (i.e., powdery), flakelike, spherical, needlelike or fibrous in shape.

The invention additionally concerns the embodiments of such methods wherein the specific reactant binding molecule is selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

The invention additionally concerns the embodiments of such methods wherein the specific reactant binding molecule has at least one binding site for the reactant, the binding site facilitating more than one reaction turnover or one reaction turnover.

The invention additionally concerns the embodiments of such methods wherein the electromagnetic field is applied at a frequency of from about 0.9 to about 25 GHz, and particularly, wherein the electromagnetic field is applied at a frequency of from about 0.9 to about 6 GHz or wherein the electromagnetic field is applied at a frequency of from about 0.9 to about 2.5 GHz. The invention particularly concerns the embodiments of such methods wherein the electromagnetic field is applied at a frequency selected from the group consisting of 0.915, 2.45, 5.85 and 22.125 GHz.

The invention additionally concerns the embodiments of such methods wherein the composite is in the form of a particle or a planar substrate.

The invention additionally concerns a composite comprising a solid material responsive to dielectric heating and a binding molecule capable of specifically binding a reactant molecule.

The invention additionally concerns the embodiments of such composite:
 1. wherein the solid material is selected from the group consisting of carbon, charcoal, amorphous carbon, carbon black, clay, and nickel;

2. wherein the solid material is an oxide selected from the group consisting of copper oxide, chromium oxide, silicon oxide, niobate oxide and manganese oxide 3. wherein the solid material is a titanate selected from the group consisting of barium titanate, and an inorganic titanate;

4. wherein the solid material is an alumina compound selected from the group consisting of alumina-magnetite, aluminum-epoxy composite and calcium aluminate;

5. wherein the solid material is an oxide or non-oxide ceramic, a ferrite, a ferroelectric polymer, or an organic polymer; and/or 6. wherein the solid material is selected from the group consisting of SiC, Si, Mg, FeSi, $Cr_2O_3$, $Fe_3O_4$, $MnO_2$, NiO.

The invention additionally concerns the embodiments of such composite wherein the solid material is a mixture of a conductive material and an insulator, and especially wherein the conducting powder is Nb, TaC, SiC, $MoSi_2$, Cu, or Fe, and the insulator is $ZrO_2$, $Y_2O_3$, or $Al_2O_3$. The conductive materials may be metals, and may be granular (i.e., powdery), flakelike, spherical, needlelike or fibrous in shape.

The invention additionally concerns the embodiments of such composites wherein the binding molecule is selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

The invention additionally concerns the embodiments of such composites wherein the composite is in the form of a particle or a planar substrate.

The invention additionally concerns the embodiments of such composites wherein the composite additionally comprises a porous, thermally-insulating coating, and particularly wherein the coating covers the solid material and the binding molecule.

The invention additionally concerns the embodiments of such composites wherein the binding molecule is bound to the solid material and the porous coating covers the binding molecule, the porosity of the coating allowing for the reactant to contact the binding molecule.

The invention additionally concerns the embodiments of such composites wherein the composite additionally comprises a specific reactant-binding molecule bound to the specific reactant and/or wherein the coating covers the solid material and the binding molecule. The invention additionally concerns the embodiments of such composites wherein the binding molecule is bound to the solid material and the porous coating covers the binding molecule, the porosity of the coating allowing for the reactant to contact the binding molecule.

The invention additionally concerns the embodiments of such composites wherein the binding molecule is selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid and/or wherein the thermally-insulating material is selected from the group consisting of cross-linked dextran, gelatin, agarose, polyacrylamide, poly acrylates, silica, and poly(styrene-divinyl benzene).

DEFINITIONS

Accelerate: To increase the rate of a chemical reaction, preferably by at least 10%, more preferably by at least 50%, and most preferably by at least 100% or more.

Aqueous Solution: A liquid medium that is more than 50% water by volume.

Artificial Antibody (or Receptor): A synthetically produced molecule that contains a binding pocket designed to be complementary in shape and/or charge to a molecule which it binds. It may be made of a single molecule, such as a small organic molecule or a man-made polymer, or it may be a bulk substance such as an acrylic polymer particle or a surface of silica. The artificial biomolecule specifically binds to the complementary molecule.

Artificial Enzyme: A synthetically produced molecule that has one or more binding sites that are complementary in shape or charge to another molecule. The artificial enzyme binds to the complementary molecule and causes the bound molecule to undergo a chemical transformation.

Chemical Reaction: The chemical transformation of one or more molecules, (reactant(s)) to form one or more molecules (product(s)).

Composite: A solid made of two or more distinct types of materials or molecules.

Dielectric Heating: Heating of a dielectric (electrically-insulating) material by electromagnetic radiation in the wavelengths between approximately 5 cm and 100 m.

Lossy Material: A (dielectric) material that loses absorbed microwave energy in the form of heat.

MATTR: "Microwave-Accelerated Targeted Triggered Reaction" technology.

Microwave: Electromagnetic radiation in the range of $10^8$ to $10^{11}$ Hz (1 m to 1 cm). Dielectric heating occurs in this range, but also occurs at longer (radio) wavelengths (up to 100 m), which could be alternatively used. Overall, dielectric heating frequencies span wavelengths of about 5 cm to 100 m.

Microwave Oven: A device that emits microwave radiation at a pre-determined wavelength into an internal chamber. The chamber is sealed to limit the escape of microwaves.

Molecular Imprinting: A process whereby specific binding sites to a chosen target (imprint) molecule are introduced into synthetic materials. The binding material is usually an organic polymer. Typically, functional and cross-linking monomers are co-polymerized in the presence of the imprint molecule, which acts as a molecular template. Subsequent removal of the template molecule reveals binding sites that are complementary in shape and size to the imprint molecule. In this way, molecular memory is introduced into the polymer, enabling it to re-bind the imprint molecule with high specificity.

Organic Solution: A liquid medium that is more than 50% organic solvent by volume.

Porous: A solid material containing channels through which water and other liquid molecules can pass.

Thermal Proximity: The situation in which one substance is close enough to a second substance to permit substantial heat transfer to occur between them. In preferred embodiments, the first and second substances are bathed in an aqueous or organic liquid solution. In many instances, the bulk of the cooler substance is not in thermal proximity with the first substance and thus does not receive substantial heat transfer.

Thermocouple: A sensor for measuring temperature consisting of two dissimilar metals, joined together at one end. The metals produce a small unique voltage at a given temperature. The voltage is measured and interpreted by a thermocouple thermometer.

Zeolite: Porous inorganic solids used in catalyzing chemical reactions. Zeolites are rigid structures based on regularly repeating patterns of aluminate and silicate tetrahedral linked by oxygen atoms.

DETAILED DESCRIPTION OF THE PREFERRED EMBODIMENTS

Background

Enzymes, Antibodies, and Uncatalyzed Reactions

Often it is desirable to accelerate the specific reaction of a single chosen chemical in the presence of other non-chosen chemicals. In a preparative chemistry example, in drug manufacture it is often desirable to accelerate a chemical reaction (for example, ester hydrolysis) of one enantiomer in a bulk racemic mixture. In an analytical chemistry example, in medical diagnostics it is desirable to accelerate a specific chemical reaction to signal the presence of one specific type of molecule in a vast milieu of other types of molecules. These are just two of many examples of specific acceleration of chemical reactions in the presence of admixture of types of molecules. An improved means of accelerating specific chemical reactions would have many practical applications in both preparative and analytical chemistry.

Reactions of analytical utility include those that result in a change in color, luminescence, fluorescence, electrochemistry, or any other detectable physical property. Preparative reactions are too numerous to list, but include hydrolysis and/or enantioselective reactions. Any preparative reaction in aqueous solution is amenable to the described method.

Nature's best-known method of accelerating specific chemical reactions is by the use of enzymes. Enzymes are proteins that act as catalysts through a two-step process. In the first step, the reactant ("substrate" (S)) reversibly binds to a specific area of the enzyme called the "active site" to form a non-covalent complex (ES). In the second step, the enzyme causes an acceleration of a specific chemical reaction of the substrate to form product (P). The process can be shown as follows;

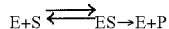

The second step (chemical step) requires energy to pass a free energy barrier. The highest point in the free energy barrier is the transition state of the reaction—the most energetically unfavorable point along the reaction pathway. Enzymes function by tightly binding to and stabilizing the transition state. Transition state stabilization lowers the free energy barrier and encourages the reaction to proceed to form product. Thus, enzymes act by using binding energy to reduce the amount of free energy required of pass the free energy barrier.

Uncatalyzed reactions also pass free energy barriers. In the absence of a catalyst, such as an enzyme, to lower the free energy barrier, such reactions may be energetically highly unfavorable. However, uncatalyzed reactions may also be accelerated. Even though the free energy barrier is not lowered in an uncatalyzed reaction, the transition state of a reaction can still be reached with high frequency by external addition of energy into the reaction. Most commonly, uncatalyzed reactions are accelerated by the input of heat. Thermal energy causes the reactant molecules to more frequently reach the energy of the transition state and to pass the free energy barrier to form product. The process of an uncatalyzed reaction is as follows (R is reactant, P is product),

Antibodies, like enzymes, are proteins. However, unlike enzymes, antibodies do not accelerate chemical reactions. Enzymes specifically bind to the transition state of a reaction, causing reaction rate acceleration. Antibodies on the other hand bind to the ground state of a chemical reaction. Because of this, antibodies do not lower the free energy barrier of a chemical reaction and hence do not enzymatically accelerate chemical reactions. Moreover, antibodies have no mechanism by which they can supply external energy (such as heat) to accelerate chemical reactions. Hence, antibodies merely bind to specific substances and do not cause chemical reaction rates to accelerate. The process of antibody (Ab) binding to antigen (Ag) is as follows;

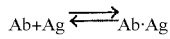

The Challenge: how to Combine Specific Ground State Binding with Directed Thermal Energy to Create "Artificial Enzymes?"

Many scientists have attempted to design artificial enzymes by making molecules with binding complementarity to the surmised transition state of a chosen reaction. The designer artificial enzymes have included catalytic antibodies, catalytic plastic polymers, and catalytic small molecules. However, none of these methods has proven to show widespread practical application. One major reason is the difficulty of making catalysts that are precisely complementary to hypothetical reaction transition states that are highly unstable and cannot be isolated or directly observed.

As seen from the discussion above, an alternative way of making artificial enzymes could be to combine the exquisite binding specificity of antibodies with the external input of some form of energy such as heat. The difficulty with this approach is that the added energy must be directed to the bound reactant. If heat, for example, is simply added to the reaction mixture, it will indiscriminately cause acceleration of all chemical reactions equally. Thus, the key challenge, which is overcome by this invention, is the directing of applied energy to specifically bound reactants. The energy is specifically directed to the bound reactant as follows (B is binding molecule (such as an antibody or plastic polymer), R is reactant, Δ is heat (energy), and P is product);

Dielectric Heating

Until recently in the history of mankind, conventional bulk heating (fire, etc.) was the only method of causing temperature increases (and acceleration of chemical reactions). In the past half century, a new fundamentally distinct form of heating has been developed called dielectric (microwave) heating. In dielectric heating, microwave radiation is applied to a sample. Compounds within the sample that are dielectrics that absorb microwaves of the applied frequency undergo increases in temperature. Dielectric materials have unique spectral characteristics of frequency versus heating ability, with different substances heating more effectively at different frequencies. The most important aspect is that in contrast to conventional heating, where the heat is applied from the outside and moves inward, in dielectric heating, the heating is directed to materials with characteristically appropriate dielectric properties. Although dielectric heating is referred to here as microwave heating, dielectric heating can also occur at radio frequencies. This invention is intended to include those effects.

According to the Arrhenius equation, the rate of a reaction can increase from a decrease in the activation energy (i.e., a change in the reaction mechanism, as with enzymes) or from an increase in the pre-exponential factor, which reflects the frequency and efficiency of collisions between reacting particles. The second reason is closely related to the mechanism of action of microwaves on substances and is major reason for a considerable acceleration of chemical processes in a microwave field (Kubrakova, 2000)

Dielectric heating depends on a number of factors including the frequency of the microwave irradiation and the absorption properties of the dielectric at that frequency. All dielectric materials have characteristic absorption spectra (frequency vs. heating ability). For example, in a conventional kitchen microwave oven, the microwave frequency (2.45 GHz) is very good for heating water, but not good for heating other materials (for example, an cup that holds the water). If the frequency of the microwave emission would be changed, in theory one could heat the cup but not the water (depending on the relative dielectric absorption characteristics of water and the cup). Thus, it is possible to heat materials in water without heating the water using dielectric heating. Of course, once the material is heated, heat will transfer into adjacent water unless the heated material is covered with a heat-insulating layer.

The dielectric is chosen (initially by literature or screening of compounds), covered by binding molecules (for example by covalent attachment, adsorption, entrapment (inside the macroporous or mesoporous insulating layer), etc., this layer may be coated with a porous layer. The dielectric is added to an aqueous or organic solution of reactant. Microwave irradiation occurs, and the appropriate product is formed.

Physical Components of a Preferred Embodiment of the Invention:

The physical components of a preferred embodiment of the invention are:

1) A microwave/radio frequency source. The reactions are preferably carried out within a chamber of a microwave generator. The microwave emission can be in the range of 300 MHz to 300,000 MHz (approx. 3 m to 3 cm). Dielectric heating also occurs at longer (radio) wavelengths (up to 100 m), which can be alternatively used. Overall, dielectric heating frequencies span wavelengths of about 3 cm to 100 m. Dielectric heating in this range is considered part of this invention. The exact frequency used would depend on the dielectric material to be heated. The dielectric would be substantially lossier than the solvent at the chosen frequency.

Attractive frequencies for this invention are 0.915 GHz, 2.45 GHz, 5.85 GHz, and 22.125 GHz. The U.S. Government currently approves these frequencies for use for industrial, scientific, and medical uses (Boon & Kok, 1989). Other frequencies may also be attractive provided that the emission within the microwave chamber is sufficiently shielded (to prevent interference with communications uses of microwaves). "Frequency-tunable" microwave ovens can be made and used for this invention (Microwave Research Center, Eagan, Minn.; Microwave Research & Applications, Inc., Laurel, Md.). Most commercially available microwaves, including home kitchen microwaves emit at 2.450 GHz, although other frequencies are freely available commercially. For example, Microdry, Inc. (Crestwood, Ky.) and Cober Electronics (Norwalk, Conn.) sell 0.915 GHz microwaves. Of the above-listed frequencies, 0.915 GHz may be most attractive for aqueous applications because water is least susceptible to dielectric heating at this frequency (Laslo, 1980);

| Relative Loss Factors for distilled $H_2O$ (Susceptibility to Microwave Heating) | | |
|---|---|---|
| 0.915 GHz | 2.450 GHz | 5.800 GHz |
| 1.4 | 11.3 | 4.3 |

It is envisioned that the reactions can be carried out with the dielectric/binding composite submerged in a liquid reaction mixture inside a microwave-generating oven. The reactant of interest will preferably be in the solution. By applying microwave heating to the dielectric in the reaction mixture, multiple turnovers (catalysis) will be possible at the liquid/solid interface.

Alternatively, if multiple turnovers are not required, the dielectric/binding molecule solid support could be removed from solution after a time sufficient for the solid phase to capture the desired reactant. Then, microwaves could be applied to the dielectric/binding composite (for example, in air). Because the bulk solution would be gone, the reaction would occur in the specific binding sites without multiple turnovers. This type of non-catalytic reaction is useful in analytical applications (for example in medical diagnostics). In diagnostics, the reactant solution might contain a biological fluid from a patient. Following capture of the desired molecule, detection can be facilitated by a microwave-accelerated reaction. For example, microwaves could cause a color change in the analyte. Alternatively, a signaling molecule, such as a labeled anti-analyte antibody can be added. The label on the antibody could undergo a reaction upon microwave irradiation to form a colored or fluorescent indicator.

Figure 1:
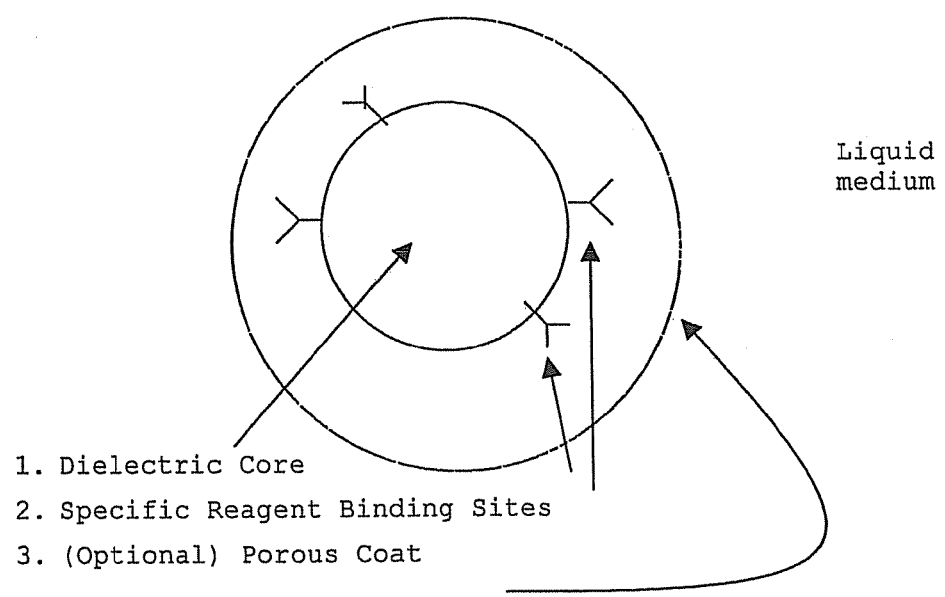
FIG. 1: Particle-based material for directed microwave chemistry. The two relevant features are: (1) a dielectric particle/bead that absorbs microwaves at frequencies different from any surrounding solvent (aqueous or organic solvent), and (2) a binding surface that specifically captures the reactant of choice. The particle also has the optional feature of a porous thermally insulating coating to reduce heat transfer from the dielectric to bulk solvent. In practice, many beads may be used (millions or more). The beads can be suspended in a liquid medium containing the reagent(s). The particles and the medium would be subjected to microwave frequency irradiation within the chamber of a microwave oven. In some applications, the particles could be removed from solvent prior to microwave irradiation.
Figure 2:
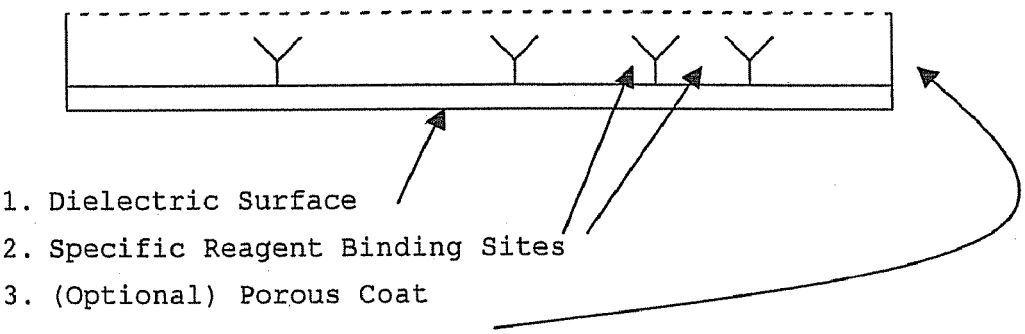
FIG. 2: Planar surface-based material for directed microwave chemistry. The relevant features are as described in the description of FIG. 1. The diagram shows what is enclosed in a microwave oven chamber during a preferred reaction. In some applications, the planar surface can be removed from solvent prior to microwave irradiation.
Figure 2:
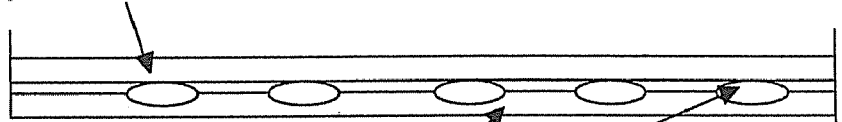
Figure 2:
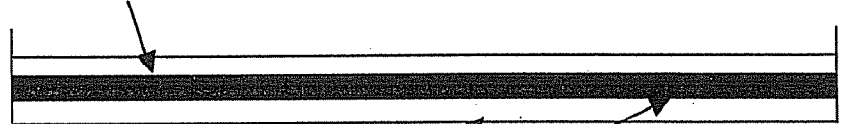

2) A Dielectric Material. The dielectric material will preferably be a solid support in contact with the liquid reactant solution. The support may have any of a variety of geometries. It could be a planar surface (e.g., a part of a coating or a wall of a chamber or the surface or a chip or cartridge). A suitable planar dielectric can be a chip, such as a multi-analyte disposable biological assay chip (protein chip or DNA chip). Such chips may commonly either possess the dielectric material as one or more spots on their surface, or may comprise a continuous layer (FIG. 2). Alternatively, the dielectric material could be in suspension in the form of a particle, such as a bead.

3) Molecules that Specifically Bind to the Reactant Molecules. Molecules that specifically bind to the reactant molecule will preferably be attached to the surface of the dielectric material. Such binding molecules can be, for example, antibodies (or derivatives thereof), receptors, receptor ligands, enzymes (or derivatives thereof), nucleic acids, molecularly imprinted polymers, zeolites, cavitands, or any other high or low molecular weight molecule that specifically binds to the reactant. The binding molecule is preferably thermally proximal to the dielectric material. It can be adsorbed, physically trapped, covalently bound, or otherwise associated with the dielectric material. Alternatively, a layer such as a membrane may be cast or placed over the dielectric, so as to be in contact with it. For example, nitrocellulose or nylon membranes can be used to capture DNA (FIG. 2c). Capture reagents (antibody or DNA, etc.) are adsorbed to the membrane in spots. A variety of membranes are available that could be used. Particles bearing capture reagent are often entrapped in the membranes (Jones, 2001).

4) An Optional Porous Thermally Insulating Layer. Optionally, a porous thermally insulating layer may be provided to contact or surround the dielectric/binding molecule layer. This layer would allow passage of reactant molecules, but would diminish the bulk transfer of heat from the dielectric material to bulk water or other solvent. For example, this insulating layer could be macroporous or mesoporous. In at least one example, molecularly-imprinted polymers, the insulting layer and the binding molecule could be the same.

5) An Optional Special Container. A functional alternative to the optional porous thermal insulating layer is to have an optional special container that holds the reaction solution. The container is "special" in that it cools the solution. The container lining may therefore contain a Peltier cooling device or an ice-water lining, or another means of withdrawing heat from the bulk solution. The effect of such a cooling container is to allow microwave heating to be more selectively directed to the dielectric material, and less toward the bulk solution. Heat transferred from the dielectric to the bulk solution would be transferred to the cooled container lining. Cooling containers are well known in many instruments, such as spectrophotometers used in cryospectroscopic work.

6) An Optional Monitoring Method. The reaction may be monitored by following a physico-chemical change that accompanies the formation of product(s) from reactant(s). The monitoring method can be a change in color, fluorescence, luminescence, mass, or any other detectable property. The chosen detection method is highly dependent on the reaction of choice and the scale of the reaction. Suitable detection methods are well known.

7) Additionally, in some cases it may be desirable to monitor and/or control the temperature of the dielectric. A thermocouple can be used to measure the temperature of the dielectric provided that the dielectric is structurally amenable (for example a chip-based dielectric. One example is if the dielectric is coated on a disposable chip (i.e., a microscope slide). A thermocouple could be used to contact the chip and monitor the temperature during heating. Moreover, thermocouple temperature measurement could be used to control the temperature by controlling the power of the microwave oven. If the dielectric temperature reached a certain level, say 300° C., the microwave could be automatically shut off. When the temperature dropped, to say 290° C., the thermocouple would cause the microwave to begin heating again. Such thermocouple-based temperature control is well known art (Huhmer and Landers, 2000; ASTM, 1993; Kreider, 1989). Alternatively, temperature can be measured using non-contact spectroscopic techniques (Slyanev et al., 2001). Both thermocouples and spectroscopic methods have been used to measure microchip temperatures (Huhmer and Landers, 2000; Slyanev et al. 2001).

Thus, the main variables in the invention are: (1) the microwave conditions used (frequency, time, power, etc.), (2) the material composition of the dielectric, (3) the reaction to be carried out, and (4) the molecule that binds to the reactant. In addition, the option of a porous insulating layer may be considered. Each of these could be different for different applications. Each variable will be discussed separately:

1) The microwave frequency: The parameter that describes the ability of a dielectric material to convert electromagnetic energy into other forms of energy (heat) is the dissipation factor or loss tangent (Tan $\delta$). For every material, Tan $\delta$ is frequency dependent. Materials that have much higher values of Tan $\delta$ than the chosen solvent (at a given frequency), are attractive for this invention. The frequency can be chosen to optimize the ratio: Tan $\delta_{dielectric}$/Tan $\delta_{solvent}$. Thus, for the invention to reach its fullest potential, the microwave frequency, and the absorbing characteristics of the dielectric (desired high absorbing) and solvent (desired low absorbing) must be optimized. In applications where multiple turnovers (catalysis) are desired, microwave irradiation can be made to occur while the dielectric is bathed in the reactant solution and the Tan $\delta_{dielectric}$/Tan $\delta_{solvent}$ ratio possesses greater relevance. If multiple turnovers are not desired (i.e., a reaction that is less than or equal to stoichiometric), the dielectric can be removed from the solvent prior to microwave radiation. Thus, when microwaving in air, for example, the Tan $\delta_{dielectric}$/Tan $\delta_{solvent}$ ratio becomes irrelevant.

2) The dielectric material: As described in 1), for aqueous reactions it is desirable to use dielectric materials that have higher loss tangents than the solvent (if catalysis is desired). A list of materials that have higher values of Tan $\delta$ than water (as a solvent) is shown below. All of these materials (and others not listed) can be used in the invention (note: investigator-to-investigator differences are usually due to differences at which the data were collected):

| Frequency | Tan$\delta$ (water) | Tan$\delta$ (dielectric) |
|---|---|---|
| 3 GHz | 1570 | ethylene glycol 10,000 |

| Effect of microwave heating on temperatures of solids - 1 min heating: | | |
|---|---|---|
| Water: | (560 W, 2.45 GHz oven) 81 C. | |
| Carbon: | (500 W, 2.45 GHz oven) 1283 C. | |
| Nickel: | (500 W, 2.45 GHz)384 C. | |
| Copper oxide: | (500 W, 2.45 GHz)701 C. (0.5 min heating) | |

| Material* | Tan$\delta$ 915 MHz | Tan$\delta$ 2450 MHz |
|---|---|---|
| barium titanate | 0.20 | 0.30 |
| clay (20% water) | 0.47 | 0.27 |
| manganese oxide | 0.09 | 0.17 |
| water | 0.043 | 0.12 |

*Buffler and Risman, 1996

A material with a high dielectric constant is barium titanate ($BaTiO_3$). The dielectric constant is 200-16,000 (compared with 80 for water). Barium titanate can be formed into films and has been used in analytical devices (Ewart et al, U.S. Pat. No. 5,922,537). Moreover, in addition to barium titanate, methods for forming thin and thick films of other ferroelectric materials at low temperature have improved steadily. Known high dielectric constant inorganic titanates, niobates, and ferroelectric polymers can be formed by many processes including low temperature chemical vapor deposition, laser photo-ablation deposition, sol-gel processes, RF magnetron sputtering, screen printing and firing, (in the case of the polymer) spin coating, and other methods (Yang et al., 1998).

Natural clay can also be used as a moldable dielectric (see tables above). In addition, a 1:1 w/w mixture of alumina-magnetite ($Al_2O_3$—$Fe_3O_4$) can be used as a dielectric support that heats strongly (Bram et al., 1991). Clay differentiates itself from water as a microwave absorber at 915 MHz much more than at 2450 MHz (compare in Table above).

Another material that could be used is carbon. The use of carbon as the dielectric is described elsewhere in this document.

Many additional dielectric materials can be identified by screening dielectrics for their ability to heat substantially faster than solvents such as water during microwave irradiation. Class I dielectrics (dielectric constants typically less than 150) and Class II dielectrics (dielectric constants typically in the range of 600-18,000) can be used (technical brochure, Novacap, Inc., Valencia Calif.). Other suitable materials include organic polymers, aluminum-epoxy composites, and silicon oxides. The microwave frequency can be varied as well. This simple screening procedure would yield conditions (frequency and material) that would direct heating toward the dielectric material without substantially heating water. Indeed, a company, Symyx Technologies, Inc. (www.symyx.com) routinely carries out combinatorial synthesis of novel materials to discover those with attractive qualities such as unique dielectric properties (Schultz et al., U.S. Pat. No. 5,985,356).

Still other materials that heat substantially under RF irradiation include ferrites and ferroelectrics.

Other types of materials that are well known to heat dramatically under microwave irradiation are various ceramics; oxides ($Al_2O_3$, for example), non-oxides (CrB and $Fe_2B$, for example), and composites ($SiC/SiO_2$, for example). Numerous materials are processed (sintered, etc.) by exploiting their microwave heating characteristics. (National Academy of Sciences USA, 1994).

Composite materials can be heated by microwaves. For example, materials that are normally transparent to microwaves can be heated by adding polar liquids or conducting particles. Refractory oxides such as alumina, mullite, zircon, MgO, or $Si_3N_4$ have been made to couple effectively with microwaves by the addition of electroconductive particles of SiC, Si, Mg, FeSi, and $Cr_2O_3$. Oxides of $Al_2O_3$, $SiO_2$, and MgO have been effectively heated by the addition of lossy materials such as $Fe_3O_4$, $MnO_2$, NiO, and calcium aluminate. Mixtures of conducting powders, such as Nb, TaC, SiC, $MoSi_2$, Cu, and Fe, and insulators such as $ZrO_2$, $Y_2O_3$, and $Al_2O_3$, have coupled well with microwaves. Various materials in solution (zirconium oxynitrate, aluminum nitrate, and yttrium nitrate) that are good couplers have also been added to enhance microwave absorption of powdered insulating oxides.

Addition of conductive materials in various shapes including powder, flake, sphere, needle, chip, or fiber, would cause the heating of low loss materials. For example carbon black or metal pieces with sizes ranging from 0.1-100 μm can increase the heating properties when used as inclusions. The nature and concentration of such materials can be optimized without undue experimentation. (Committee on Microwave Processing of Materials et al., 1994)

3) The reaction carried out could be virtually any chemical reaction in which the reactant(s) can be bound to a specific binding reagent. These include all known enzyme-catalyzed reactions and all known zeolite reactions. It also includes reactions not know to be catalyzed by natural catalysts. The key features are; (1) the reactant(s) be able to be specifically bound, and (2) the reaction be accelerated by heat.

4) The reactant binding molecule can be any molecule that is capable of specifically binding the reagent(s). If more than one turnover is required, then the binding molecule should also be heat stable. The molecule may be low or high molecule weight, natural or manmade. Typical binding molecules could be molecularly-imprinted polymers and zeolites. Any of a variety of modes of attachment to the dielectric can be employed. For example, molecularly-imprinted polymers can be polymerized around dielectric beads or particles. Alternatively, molecularly-imprinted polymers can be formed as thin layers on surfaces (Shi et al., 1999; Glad et al., 1985; Kempe et al., 1995; Burow and Minoura, 1996; Mathew-Krotz and She, 1995; Dai et al., 1999; Norrlow et al., 1984). Zeolite crystals can be grown on dielectric surfaces or be coated by the technique of dip coating (van Bekkum et al., 1994; Jansen et al., 1994).

5) The optional porous layer can be any material that permits the passage of reactants and products and has some thermal insulating properties. Essentially, the purpose of this layer is to slow heat conduction from the dielectric to the bulk aqueous phase. This layer may not be necessary, especially if the amount of dielectric is small compared to the volume of water. Many types of porous materials are polymers.

In general, the porous layer can be any material that allows the reactant(s) to pass through pores in its surface to reach their specific binding sites. The porous layer should be made from a material that has thermal insulating properties, although any ability to slow diffusion of water will be beneficial. Some materials that could be used are organic polymers, which could be crosslinked or formed on the surface or adsorbed and crosslinked dextran, gelatin, or agarose. Others include synthetic polymers such as acrylates, polyacrylamide, silica, and poly(styrene-divinylbenzene).

Preferred Methods and Compositions of Matter

There are numerous ways of practicing the present invention. Some variables include: altering the microwave frequency and power, altering the identity of the microwave susceptible material, altering reaction surface shape (planar or spherical), altering the reagent capture mechanism (antibodies, DNA, covalent, non-covalent, etc), and altering the identity of the reaction to be accelerated, and practical applications (analytical, bioanalytical, preparative, etc.). Described below is an overview of some variables and their practical application. Also described are the current best ways of carrying out the microwave accelerated targeted reactions.

One highly attractive format for the invention is to use it on "chips," i.e., disposable planar surfaces, often made on microscope slides (for example, 1×3 inch rectangles of glass or 5 inch×5 inch plates of glass). By spotting using jet printing or other fine depositions methods results in from one to thousands of reaction spots. As shown in FIG. 2, the chips can have the microwave-susceptible material on the chip either by various shapes including spotting or by having a contiguous layer. Small volume analyses on such so-called "microchips" (Schmalzing et al., 2000) enable huge numbers of assays to be performed on a single chip. Arrays, or "microarrays", on chips can be used for analytical purposes. Thousands of assays can be performed on a single chip using deposition technologies know in the art which are commercially widely available (Pasinetti, 2001; Lennon, 2000; Cooper, 2001; Draghici, 2001; Zubritsky, 2001). For example, an array of spots can be used to detect genetic mutations in a myriad of genes. Chips made employing the present invention can be used in numerous analytical applications including but not limited to; biochemical research, medical diagnostics, water testing, food pathogen testing, and chemical/biological warfare agent testing.

Other uses for chips are in the field of combinatorial chemistry (Dolle, 2000). Numerous unique chemical compounds can be synthesized in situ on chips. For example, thousands of different peptides could be prepared by conventional solid phase procedures on a chip. The combinatorial chemistry chips could then be used analytically to assay the solid phase chemical libraries. For example, the chip could be exposed to an solution of chemiluminescently-labeled enzyme solution and binding could be detected. Such an assay format could be used to discover enzyme inhibitors. Similarly, receptor binding to combinatorial libraries of potential ligands could be conducted.

The chips (or alternative dielectric surface) can also be coated with material for solid phase extraction of analytes from a bulk solution. Solid phase extraction can be non-specific (adsorption), immunoabsorption, or by using molecularly-imprinted polymers (Fleisher & Boos, 2001; Krishnan & Ibraham, 1994).

Many attractive potential uses of microwave targeted reactions are in the fields of biotechnology/medicine. In these cases, measured analytes have biological function. Any conventional assay such as an immunoassay or a DNA probe assay can be carried out by the described technology. In these assays, well-known chemical conversions would occur causing a detectable physicochemical change in some label. For example, chromogenic, fluorogenic, or luminescent reactions.

Yet another assay format that could be used is molecular beacon technology (Robinson et al., 2000). With molecular beacons, hybridized strands of nucleic acid are detected by fluorescence emission and quenching by end-labeled nucleic acid probes. One end has a fluorophore, the other a quencher. Upon hybridization the ends separate and fluorescence is detectable. Using microwave heating, the probe could be released back into solution at a temperature. The temperature of separation (melting temp) could be determined by fluorescence quench upon release. The most attractive detection format is chemiluminescence (CL). These are described in greater detail below in the section delineating sample practical applications in medicine.

A preferred way of conducting the procedure is to use carbon particles as the dielectric. Carbon may be activated carbon/charcoal (Sigma-Aldrich Chemical Co.), carbon black (Columbia Chemicals, Marietta, Ga.; Reade Advanced Materials, Providence, R.I.), graphitized carbon particles (Polysciences, Inc. Warrington, Pa.) or dextran-coated charcoal beads (Research Diagnostics, Inc.). Preferably the carbon beads are coated with a polymer that is imprinted with the reactant (ideally, polymerized around the carbon).

Microwave chemistry is a field where chemical reactions are accelerated using microwave radiation, rather than conventional bulk heating. In those inventions, the bulk medium is usually heated. The bulk medium is usually not aqueous, but organic solvent. In no case has specific binding been a component of the heating. Additionally, heating has not been directed to a solid dielectric material to selectively react proximal reactant molecules.

Often, it is desirable to accelerate the specific reaction of a single chosen chemical in the presence of other non-chosen chemicals. In a preparative chemistry example, in drug manufacture it is often desirable to accelerate a chemical reaction (for example, ester hydrolysis) of one enantiomer in the presence of a mixture of types of molecules (for example, a bulk racemic mixture). In an analytical chemistry example, in medical diagnostics it is desirable to accelerate a specific chemical reaction to signal the presence of one specific type of molecule in a vast milieu of other types of molecules. The present invention provides an improved means of accelerating specific chemical reactions, and as such has many practical applications in both preparative and analytical chemistry.

Reactions of analytical utility include those that result in a change in color, luminescence, fluorescence, electrochemistry, or any other detectable physical property. Preparative reactions include hydrolysis and/or enantioselective reactions, etc. Any preparative reaction in aqueous or organic solution is amenable to the described invention. As with analytical applications, preparative reactions can be monitored by changes in color, luminescence, fluorescence, or any other detectable physical property.

A preferred reaction is the chemiluminescent reaction between luminol and hydrogen peroxide. As described below, this reaction is a well-known signaling reaction used in various fields such as medical diagnostics and biomedical research. The reaction is temperature dependent and can be slowed to appropriate temperature control by adjusting the pH to a point lower than optimal (see Example 9).

Chemiluminescence reactions, such as the luminol-peroxide reaction, can be monitored and quantitated in many ways including the use of film (for example, X-ray film), or electronically using a photomultiplier tube (PMT) or a charge-couple device (CCD) camera. A PMT-based instrument would involve a microwave oven with a window through which light is measured. Measurement using a PMT or a CCD camera would be collected and analyzed using a personal computer and conventional commercial data acquisition/analysis software (for example, LabVIEW). Currently a preferred method involves the use of film.

As described above, the dielectric material can be in various formats. Currently the most attractive format is on a chip, either as spots or as a layer. The use of a "dielectric chip" allows sensitive detection of multiple analytes. Indeed, microarray chips or microchips are an attractive application of the invention.

Description of Illustrative Practical Applications

There are numerous practical applications of targeted triggered microwave reactions. Many are in the fields of analytical and preparative chemistry. Some though, are in non-analytical fields. For example, a reaction could be directed at a toxin (such as a nerve gas) to specifically inactivate that toxin. The described invention could be useful in any practical application where a chemical reaction is desired and it is important that that reaction is specific for the chosen molecule.

Very attractive applications are in the biomedical analysis. Analyses of biomolecules are critical to diagnostic/prognostic evaluations. Moreover, scientific research depends on the ability to detect and measure specific biomolecules. Such biomolecules include but are not limited to proteins (immunoassay detection) and nucleic acids (hybridization detection).

Comparison with Alternative Technologies

Microwave-accelerated chemiluminescence (CL) analysis in a medical or research setting has several advantages over commonly used technologies. Microwave-accelerated CL-based analysis on chips is termed herein as "Microwave Accelerated, Targeted, Triggered Reaction" technology (MATTR).

MATTR technology represents the first use of directed microwave chemistry in biotechnology. As a breakthrough bioanalytical tool, MATTR has clear advantages over existing methods. There are two types of comparable technologies;

First are mainstream chemiluminescent analytical technologies (Bowie et al., 1996; Roda et al., 2000). Companies marketing these technologies include Tropix (subsidiary of PE Corp.), which sells enzyme-based CL reporters, and Amersham Pharmacia Biotech, which sells CL-based gel blotting detection systems. Other companies with conventional CL-based products include Lumigen, Lifecodes, Vector, Invitrogen, and Pierce. The attractiveness of MATTR over conventional analytical CL methods can be seen in Table 1. CL reactions are generally either "flash type" or "glow type". Flash-type reactions are instantaneous and hence demand fast reagent mixing and analysis. Glow-type CL reactions emit low levels of light over a long time period (minutes or hours).

Highly sensitive and extremely rapid analysis. Rapid, targeted microwave heating caused by causes a burst of CL light, using well-established highly-sensitive CL chemistry.

A technology capable of multiplexed, microchip-based assays. Microwave heating can be spatially directed, e.g., to specific areas on a microarray chip by patterned dielectric spots. A broadly enabling technology, useful for many types of assays. Because MATTR incorporated well-established luminescent labels, it will be able to be used in all formats of conventional CL, as well as more. It promises to be useful in immunoassays as well as DNA probe assays.

TABLE 1

Comparison of Flash and Glow CL reactions to MATTR-based CL reactions

| Flash | | Glow | | MATTR | |
|---|---|---|---|---|---|
| Advantages | Disadvantages | Advantages | Disadvantages | Advantages | Disadvantages |
| Rapid time to answer | Timing of injection, read | Substrate addition non-critical | High temperature dependence | Substrate addition non-critical | Requires microwave source |
| High-throughput | Mixing critical | Signal can be adjusted for different enzyme levels | Amplifies background & non-specific binding | High-throughput | |
| High signal-to-noise | Photon counting more difficult | Read time can be adjusted to increase high-throughput | Signal generation is affected by assay additives | High signal-to-noise | |
| Low temperature dependency | Difficult to engineer signal variations | Easy to engineer | Stable signal can take hours | Easy to engineer | |
| Linear response | | Samples can be sequentially read | | Linear response | |
| Wide dynamic range | | | | Wide dynamic range | |

A typical glow type reaction involves the hydrolysis of chemiluminescent dioxetane compounds. As shown in FIG. 3, hydrolytic dioxetane luminescence is highly temperature dependent. Thus, dioxetanes make excellent MATTR labels. A typical flash type reaction involves chemiluminescent acridinium esters. The flash of CL of acridinium esters is chemically triggered upon mixing with chemical initiators. The reaction rate is slowed to an imperceptibly slow rate by lowering the initiator concentration. Microwave heating restores the rapid reaction rate causing a chemiluminescent flash (Wood, 1984).

MATTR technology fulfills several criteria, which distinguish it as a breakthrough bioanalytical technology and as a significant improvement to conventional CL-based bioanalyses:

A CL technology that offers signal generation "on demand" (electronically, not by reagent mixing). In MATTR, microwave energy is applied on demand, conveniently allowing CL reactions to be triggered electronically rather than by rapid physical mixing.

A physically simple analytical instrument to reduce costs and minimize maintenance. MATTR requires microwave input, which is diffuse and thus simpler than technologies that require focused light input (fluorescence or spectrophotometry).

MATTR Instrumentation in Biomedical Analyses

As described above, CL from a MATTR chip could be measured on film or electronically (using a PMT or CCD camera). If a PMT or camera is used, a "MATTR instrument" is employed. The basic components of a preferred MATTR instrument are shown in FIG. 4. The preferred instrument includes a microwave oven with a window through which chip-emitted light is detected by a PMT or camera. Onset of microwave irradiation (acceleration of CL reaction), light measurement, and data analysis are carried out, for example, using a standard PC with appropriate software. Suitable data acquisition/analysis software is common and known in the art.

One type of MATTR instrument that can be made to measure cytokines on chips is described here;

a suitable microwave oven is made from a microwave moisture/solids analyzer (model M2, Denver Instrument Co., Arvada, Colo.). The oven will preferably have a single mode microwave chamber to provide a uniform power density. The microwave chamber of such an oven is small and cylindrical and the energy is focused on the sample. The operating frequency of microwave emission will be 2450 MHz. The output power of the microwave will be 550 W. The power source will be 115 V, 60 Hz.

The interior of the oven chamber will be fitted with a chip holder that is aligned with the fiber optic cables. The fiber optics will run from the interior of the microwave to a PMT on the exterior of the oven. The chip holder will support disposable dielectric assay chips of various sizes (for example, from 1×3 inches up to 5×5 inches).

A fiber optic detection system to allow chip imaging within the microwave chamber. Fiber optics will lead from the chip to a light-recording photomultiplier tube (PMT, Hamamatsu model H5784-01), which captures light emitted light from the CL reaction, and a personal computer will preferably control and synchronize the PMT and the microwave source. The computer will also preferably run a versatile data acquisition, control, analysis, and presentation software package, such as LabVIEW software (National Instruments Corp.).

MATTR Chemiluminescent Compounds for Bioanalytical Assays

There are very many chemiluminescent reactions known which efficiently emit light and can be used for bioanalytical purposes. Some classes of CL reactions are (each of which has many structural variations); 1,2-dioxetanes, aryl oxalates, acridinium esters, luminols, and lucigenin. All of these classes have been used analytically, either as labels in immunoassays or as chemiluminescent enzyme substrates. In most cases, the light-emitting chemical reaction that occurs is a bimolecular reaction, often with an oxidizing agent. Hydrogen peroxide and sodium hydroxide are common second reagents. All of the reactions may be accelerated by an increase in temperature. There are vendors of these compounds such that both free CL compounds as well as CL compounds labeled with linkers for protein modification for use in immunoassays.

One type of CL reactant class that is very useful in MATTR CL reactions is 1,2-dioxetane reactions. Dioxetanes emit light without any secondary reagent such as hydrogen peroxide. In addition, dioxetane CL reactions are remarkably temperature dependent as is shown in FIG. 3. Dioxetanes are used as glow type regents in enzyme immunoassays and enzyme assays of alkaline phosphatase, glucuronidase, glucosidase, and beta-galactosidase (Tropix, Foster City, Calif.). As can be seen from FIG. 3, they can be converted from glow type reagents to flash type reagents by the use of elevated temperature. Various dioxetanes are commercially available from Tropix and other sources and methods for conjugating them to proteins have been published. In addition, Tropix sells conjugates, which can be linked to proteins.

Acridinium esters are another class of CL reagents that is useful in MATTR. These compounds react with acids and bases in the presence of an oxidizing agent, resulting in flash type CL. Several acridinium esters are commercially available. Lumigen, Inc. (Southfield, Mich.) sells small, water-soluble chemiluminescent labeling acridinium esters that are triggered by a simple chemical reaction to produce CL as a rapid flash. The compounds are modified to permit covalent attachment to proteins, nucleic acids, and other biomolecules. The chemical kinetics of these compounds can be slowed by judicious dilution of the triggering reagents. Flash CL will be restored upon microwave heating. Another company, Assay Designs, Inc. (Ann Arbor, Mich.), also sells acridinium ester labeling kits. Their acridinium esters link to proteins via NHS ester functional groups. Assay Designs also sells trigger solutions to affect light emission.

MATTR Chip-Based Immunoassays

MATTR-based immunoassays may be conducted in any of a wide variety of formats. For example, a MATTR chip, with specific capture molecules on it surface, may be exposed to analyte solution, followed by secondary antibody binding (if necessary), and washing (if necessary) (FIG. 5). Immunoassays are performed using either competitive or sandwich immunoassay formats. The signaling label, a low molecular weight chemiluminescent reporter molecule, will be present on the appropriate surface-bound molecule. Once the binding and washing has been completed, the chip is placed in the MATTR instrument and analysis is carried out.

Immunoassay Detection of Angiogenic Growth Factors

One application of MATTR technology is in the immunoassay-based detection of cancer-related angiogenesis proteins. Angiogenesis, also called neovascularization, occurs in the healthy body during wound healing, in the female monthly reproductive cycle, and in pregnancy. Angiogenesis is controlled in the body through a series of "on" and "off" regulatory switches—the main "on" switches are known as angiogenesis growth factors (cytokines) while the main "off" switches are known as endogenous angiogenesis inhibitors. In the healthy body, there is a balance between angiogenic and anti-angiogenic factors such that blood vessel growth is appropriate.

Tumors express large amounts of angiogenic growth factors to recruit their own blood supply. Solid tumors require a constant vascular supply, which allows cancer cells to maintain their growth advantage. Because of the relatively large amounts of angiogenesis factors secreted by tumor cells, tumor vasculature is abnormally wide lumens, irregular blood flow, regions of stasis, and high permeability. There are many different angiogenic proteins, making them attractive for multi-analyte chip based detection and measurement. Analysis of angiogenic factors is important in biomedical research and in diagnosis on treatment of various diseases, including cancer.

Anti-angiogenic therapy offers a promising anti-cancer strategy (Folkman, 1997). Angiogenesis inhibition would prevent further vessel growth and reduce metastasis, and hence inhibit tumor growth. This philosophy is being widely pursued. Currently an amazing diverse group of over 20 anti-angiogenic drugs are undergoing evaluation in clinical trials (Saaristo et al., 2000) with many more in various stages of research and development.

An example of an immunoassay is one for tumor necrosis factor alpha (TNFα). TNFα is an angiogenic growth factor protein. There are several commercial sources of high quality required reagents, TNFα and appropriate antibody pairs. R&D Systems (Minneapolis, Minn.) sells a CL-based assay for this protein that could be used in a MATTR based assay. The assay is a sandwich enzyme immunoassay. With MATTR, the secondary antibody is labeled with multiple copies of a chemiluminescent compound by means known in the art.

MATTR Chip-Based Nucleic Acid Probe Assays: Cancer Cell Gene Expression Analysis Another practical application of microwave-accelerated chemiluminescence on dielectric chips is in nucleic acid detection of cancer cells. Molecular oncology is increasingly moving toward the use of multiple biomarkers for diagnostic, and prognostic purposes (Sidransky, 1997; Abati & Liotta, 1996; Marx, 2000). The understanding of how individual tumors grow and respond to treatment is based on an understanding of how cellular molecules interact to affect cell growth, metastasis, and response to anti-tumor agents. Because cancer is a highly individual disease—it is not one disease but hundreds—it will become extremely valuable in the future to be able to detect, not just one or two tumor markers, but a large number simultaneously. The field of personalized oncology hinges on two features; 1) an understanding of the intricate molecular roles of cancer proteins, and 2) the ability to detect and measure the many key molecules, which determine the individual characteristics of tumors. MATTR can play an important role in both aspects; MATTR chips may help researchers map the pathways of tumors, and provide physicians with critical information needed to effectively custom-treat a cancer patient. In the long term, a potentially important role exists for MATTR-based gene expression profiling in cancer screening, diagnosis, staging, surveillance, and treatment monitoring.

MATTR also can be applied in the detection of assay panels in cancer staging and also in the detection of minimal residual disease (MRD). After cancer is diagnosed, the extent or "stage" of the cancer is determined before deciding on a treatment plan. Tests are performed to determine tumor staging (size/extent of tumor), node staging (involvement of lymph nodes), and metastasis staging (presence or absence of metastasis). Staging is performed in part with the use of molecular testing for tumor cells in blood and sentinel nodes. Tumor staging is a very attractive application of MATTR array testing because it allows physicians to determine treatment strategies, particularly about whether or not to prescribe adjuvant therapy.

A second foreseeable nucleic acid diagnostic application of MATTR chips is the detection of minimal residual disease (MRD). Decision of treatment would be greatly enhanced by a multi-analyte cDNA panel showing able to detect circulating cancer cells at low levels undetectable by other methods. Using MATTR, some patients in clinical and pathological remission will show evidence of "molecular disease", which has clear diagnostic and therapeutic implications. Molecular diagnostics has great potential in identifying MRD.

It is clear that future testing will involve detection and measurement of arrays of cancer-associated biomarkers. Multi-analyte panels have clear advantages over single analyte testing. With multiple markers, there is much less chance of false positives/negatives. In addition, perhaps most importantly, is that multiple biomarkers will give a clearer and more complete picture of the tumor's characteristics. For example, the likelihood of drug resistance or metastatic potential could be confidently determined. In most cancers, the ideal panels for these determinations have yet to come into focus. MATTR chip technology can also become a powerful clinical trials and basic research tool. Versatile arrays will be useful in developing important analytical arrays.

MATTR technology can be used to detect mRNA in cancer cells to determine which of several important cancer proteins are being produced. Analysis will be performed on cDNA prepared from cellular mRNA by RT-PCR. RT-PCR is a powerful and sensitive method for amplifying specific cellular mRNA (Latchman, 1995) and is becoming a powerful method for both qualitative and quantitative molecular diagnostics (Freeman et al., 1999). In RT-PCP, mRNA is isolated (either total or polyadenylated RNA). RNA is then reverse-transcribed to complementary DNA (cDNA) using the retroviral enzyme, reverse transcriptase ("rt"). Primers (gene specific or universal) are required to initiate reverse transcription. Product cDNA is amplified, as with the polymerase chain reaction ("PCR"), etc., to give detectable quantities of cDNA. RT-PCR is an established method that is often used to detect cancer gene expression (for a review, see Seiden & Sklar, 1996). In almost every published report of RT-PCR analysis of cancer gene expression, only a single type of mRNA has been detected, and detection has been via electrophoresis and detection by radiolabel or stain.

Currently, single tests of individual gene mutations and expression are used clinically in oncology for detection of tumor cells. Someday, vast cDNA microarrays will be commonly used to detect and characterize tumor cells on the level of the whole genome (Schena et al., 1995; Harkin, 2000). In the short term, smaller panels of selective tests will become extremely valuable in the sensitive detection and characterization of tumor cells. Array testing of cancer gene expression will not only provide a more reliable diagnosis, but also will offer a much more informative picture of a patient's prognosis.

Analysis of Nucleic Acids:

MATTR-based nucleic acid analysis will have much in common with immunoassays analysis by the same technology. The major differences are described here. Assays may take place as follows;

(1) A MATTR chip (FIG. 6), with specific capture molecules on its surface, is exposed to analyte solution and the analyte binds to the surface. In one type of assay, the captured analyte is detectable because it itself has been pre-labeled with CL molecules (Schena et al., 1995). The target cDNA can be labeled using any of the many well-known methods and reagents (TriLink BioTechnologies, Inc. San Diego, Calif.; Glen Research Corp., Sterling, Va.). It is preferable to label the target with multiple CL reporter groups. For example, DNA can be chemically biotinylated and the biotin-DNA molecule can bind streptavidin labeled with multiple luminol molecules (FIG. 6). Alternatively a sandwich type format can be employed in which a secondary probe is used (Kricka, 1999). In this format, the primary probe, immobilized on the chip, captures the unlabeled target molecule, which in turn captures the CL-labeled secondary probe.

The capture molecule layer is spotted on a nylon membrane (FIG. 6). The nylon may be a full-size overcoat or punched into small circles. The actual spotting process is carried out using a manual microarray spotter (Xenopore Corp.), which can deposit spots on a standard 1"×3" microscope slide. The manual microarrayer is a simple bench top device, measuring only 5"×5" and weighing less than three pounds. It requires no external power source. Uncoated or derivatized glass microscope slides, coverslips, porous membranes, gels, or plastics.

(2) Once binding has been completed, the chip is placed in a chip holder in a MATTR instrument and measurement is made. It should be noted that, as expected, the microwave-generated heat will denature the analyte, but the signal will not be affected.

Description of Analysis of a Specific mRNA

Expression of a specific cancer gene in a tumor cell line can be detected, for example, using a modification of the method of Leitzel et al. (1998) in which RT-PCR was used to detect EGFR mRNA in tumor cell lines. EGFR is a notable prognostic marker in breast cancer.

The appropriate cell line expressing EGFR is cultured (A431 epidermoid carcinoma cells (American Tissue Culture Collection, Manassas, Va.) as well as a control cell line. Appropriate hybridization primers, which could be used on a MATTR chip to demonstrate the detection of EGFR cDNA are disclosed by Leitzel et al. (1998). Total RNA is isolated from cells, and RT-PCR is performed. During RT-PCR, the cDNA is labeled with biotin by established procedures. Biotinylated cDNA is captured on a nylon-coated MATTR chip by specific primer. Luminol-labeled streptavidin is then added, which binds to the captured biotin. Addition of a small amount of peroxide and microwave irradiation results in light emission, which is detected by film or electronic means.

Having now generally described the invention, the same will be more readily understood through reference to the following examples, which are provided by way of illustration, and are not intended to be limiting of the present invention, unless specified.

EXAMPLES

Example 1

Microwaves Preferentially Directed to Carbon Particles Suspended in Water

An experiment was carried out to test whether carbon particles in water would heat substantially faster than the water they are suspended in. The experiment involved a conventional kitchen microwave oven (Panasonic NN-S949, 1100 W output, 2.45 GHZ). Carbon is known to be lossier than water at the emitting frequency. Thus, a suspension of carbon (approx. 200 mg) in water (approx. 100 mL) should heat faster than neat water. Water (100 mL) was heated in the absence or presence of ground carbon (charcoal briquettes (Super G, Landover, Md.) were ground to a powder using a mortar and pestle). After 1.0 minute of microwaving, the carbon-containing water was nine degrees warmer (83° F.) than water alone (74° F.). (The heated carbon transferred its heat to water, which I measured). The experiment was repeated and similar results (nine degrees hotter in the presence of carbon) were found. This shows that substances can be preferentially heated in water by dielectric heating. Alternatively, a different dielectric material could have been used which heated much faster than carbon at 2.45 GHz, or a different frequency could be used which does not heat water well, or both.

Example 2

Microwaves Preferentially Directed to Hydrated Clay

Three experiments were carried out to test whether hydrated clay would heat substantially faster than the water. A report by Buffler & Risman (1996) indicated that clay would heat faster than water, especially at 915 MHz. Clay is moldable and could be used as a core dielectric in beads or as a flat surface in cartridges. To test this hypothesis, a 2450 MHz emitting microwave oven was employed. Based on the report of Buffler & Risman, any positive result in these (2450 MHz) experiments would indicate that much better results could be obtained at 915 MHz.

Experiment 1: Approximately 100 mL spring water were heated in a plastic microwavable cup for 60 seconds in the same microwave as described in Example 1. The temperature rose from 25.0° C. to 92.5° C. The same volume of water, but containing approximately 200 mg clay (Bentonite 200 clay, supplied as dry powder from Great Lakes Clay and Supply Co., Carpentersville, Ill.) was also heated in the microwave. The temperature rose from 25.0° C. to 94.5° C. This experiment indicated that clay heated more than water and the temperature change in the presence of clay was due to (minor) heat transfer from the (hot) clay particles to the bulk water.

Experiment 2: Approximately 200 mL spring water was heated in a plastic microwavable cup for 45 seconds in the same microwave. The temperature rose from 19.0° C. to 49.0° C. The same volume of water, but containing approximately 50 mg clay (Bentonite 200 clay) was also heated in the microwave. The temperature rose from 19.0° C. to 52.0° C. This experiment provided verification that clay heated more than water and the temperature change in the presence of clay was due to (minor) heat transfer from the (hot) clay particles to the bulk water.

Experiment 3: Approximately 50 mL room temperature spring water was heated in a plastic microwavable cup for 30 seconds in the same microwave. The temperature rose to 68.0° C. The same volume of room temperature hydrated Bentonite 200 clay (minimal liquid water) was also heated in the microwave. The temperature rose to 84.0° C. This experiment verifies that clay heats faster than water when exposed to 2450 MHz (1100 W) microwave irradiation. It also indicates that the increase in temperature of the clay-containing water in Experiments 1 and 2 was due to (minor) heat transfer form the substantially hotter clay to the cooler water. Microwave heating was directed to clay in the presence of water.

Example 3

Preparation of Carbon-Containing Molecular Imprinted Polymer Particles that Bind L-Phenylalanine-p-Nitroanilide There are many possible physical formats in which an artificial biomolecule is in thermal proximity to the microwave-heated dielectric. One type of format is a bead or particle. In the embodiment described here, carbon particles (the dielectric) and molecularly imprinted polymer (the artificial biomolecule) are formed into composite particles.

The polymer is created from monomers and crosslinkers in a solution containing both the print (template) molecule. Also present in suspension are carbon particles. As polymerization occurs, the growing crosslinked polymer entraps both the template molecule and the carbon particles. The polymer/carbon particle composite is ground to small fragments. This, the carbon particles and imprinted binding sites in the polymer are present in close proximity.

This example describes in detail the preparation of such a dielectric/artificial biomolecule composite material. The composite can be used to selectively hydrolyze L-phenylalanine-p-nitroanilide from a mixture of L- and D-enantiomers.

Synthesis of D- and L-phenylalanine-p-nitroanilide (O'Shannessy et al., 1989a). The D- and L-phenylalanine anilides are synthesized by coupling the corresponding BOC-derivatives with aniline using 1,3-dicyclohexylcarbodiimide/1-hydroxybenzotriazole as condensation agents in N,N-dimethylformamide. After deprotection with trifluoroacetic acid, the resulting solid is solubilized with 0.1 M HCl, filtered, and extracted with toluene. The pH of the aqueous phase is adjusted to 9 by addition of 1 M NaOH and the free bases of the anilides were extracted into ethyl acetate. The free bases of the anilides are then crystallized from 1-propanol/hexane.

Preparation of Carbon Particles. Small Carbon particles can be prepared from charcoal as described in Example 1 above. Alternatively, activated carbon (Darco® KB, 100 mesh, Aldrich Chemical Co., Milwaukee, Wis.) can be used. In either case, the carbon is ground using a mortar and pestle to create fine particles. The carbon particles are suspended in chloroform and sieved through a 10 μm sieve. The chloroform that passes through the sieve is evaporated down until a fairly concentrated suspension of carbon particles is obtained. This carbon suspension will be used as the solvent during molecular imprinting polymerization.

Preparation of Molecularly Imprinted Polymer/Carbon composites (O'Shannessy et al., 1989a; O'Shannessy et al., 1989b). The carbon particle-containing chloroform described above is used as the solvent. Into a glass 50 mL tube is added; 1.956 mmol of the print molecule L-phenylalanine-p-nitroanilide (PPNA), 7.86 mmol of the functional monomer methacrylic acid (MMA), 39.3 mmol of the crosslinker ethylene glycol dimethacrylate (EDMA), 12 mL of the solvent, and 0.57 mmol of the initiator 2,2'-azobis(2-methylpropionitrile (AIBN). The tube is sealed and full solubilization is achieved by sonication. The mixture is degassed by sonication and sparged with nitrogen for 5 minutes. The mixture is cooled to 4° C. At that temperature, the mixture is illuminated overnight using a standard laboratory UV source (366 nm) with very gentle agitation to prevent the suspended carbon particles form settling.

The formed polymer (solid) is broken into small pea-sized pieces, then ground to a powder using a mortar and pestle. The powder is suspended in chloroform, then filtered through a 100 μm sieve. Using a sintered glass funnel, the print molecule is removed by solvent exchanges. A 30:70 mixture of ammonium hydroxide ($NH_4OH$) and acetonitrile ($CH_3CN$) is used followed by $CH_3CN$ alone. Finally, the composite particles are dried.

Example 4

Microwave Hydrolysis of L-Phenylalanine-p-Nitroanilide; Molecularly Imprinted Polymer Dielectric Particles in Contact with the Reactant Solution Hydrolysis of L-phenylalanine-p-nitroanilide (L-PPNA) is carried out in the presence of the imprinted composite particles described in Example 3. The particles (0.2 g) are suspended in a 50 mL solution (0.1 mM) of L-PPNA. The L-PPNA solvent is 80% $CH_3CN$/20% $H_2O$ (water is neutral pH).

The particle/substrate solution is placed in a 1100 W/2.450 GHz microwave. Microwaves are generated for a time sufficient to accelerate the reaction at the surface of the particles. As controls, the same experiments (microwaving L-PPNA solutions) are repeated in the absence of particles.

Analysis of the quantity of p-nitroaniline is carried out, either by spectrophotometric or HPLC analysis (both types of analyses are know to those skilled in the art). Results show that more p-nitroaniline is generated in the presence of particles.

To show that microwave hydrolysis is not a result of non-specific binding of L-PPNA to the particles, the experiments are repeated with D-PPNA. The results show that, under identical conditions, more L-PPNA is hydrolyzed than D-PPNA. These results show that the hydrolytic binding sites have enantiomeric specificity for L-PPNA.

Catalytic molecularly imprinted polymers (artificial enzymes) have been described previously (Leonhardt and Mosbach, 1987; Bystrom et al., 1993), but this is the first description of an artificial enzyme in which catalysis is accelerated through directed heating by microwaves.

Example 5

Microwave Hydrolysis of L-Phenylalanine-p-Nitroanilide; Molecularly Imprinted Polymer Dielectric Particles in Contact with Air Hydrolysis of L-phenylalanine-p-nitroanilide (L-PPNA) is carried out in the presence of the imprinted composite particles described in Example 3. The particles (0.2 g) are suspended in a 50 mL solution (0.1 mM) of L-PPNA. The L-PPNA solvent is 80% $CH_3CN$/20% $H_2O$ (water is neutral pH).

Following sufficient time for L-PPNA to reaching binding equilibrium with the molecularly imprinted polymers, the composite particles are filtered from the reactant solution and briefly washed with water to remove excess reactant.

The filtered particles are placed in a 1100 W/2.450 GHz microwave oven. Microwaves are generated for a time sufficient to accelerate the reaction at the surface of the particles. As controls, the same experiments (microwaving L-PPNA solutions) are repeated in the absence of particles.

Analysis of the quantity of p-nitroaniline is carried out, either by spectrophotometric or HPLC analysis (both types of analyses are know to those skilled in the art). Results show that more p-nitroaniline is generated in the presence of imprinted particles than control (non-imprinted) particles.

To show that microwave hydrolysis is not a result of non-specific binding of L-PPNA to the particles, the experiments are repeated with D-PPNA. The results show that, under identical conditions, more L-PPNA is hydrolyzed than D-PPNA. These results show that the hydrolytic binding sites have enantiomeric specificity for L-PPNA.

Example 6

Preparation of a Zeolite-Coated Clay Dielectric Surface

Zeolites are porous inorganic solids used to catalyze specific chemical reactions in many applications, including the conversion of crude oil to gasoline and the in automotive mufflers to remove CO, NOx, and hydrocarbons from gaseous exhaust (Rouhi, 2000). The reactions take place within confined cavities inside the zeolites. As with any chemical reaction, reaction rates within the spaces of zeolites increase with temperature.

Zeolites can be immobilized on porous and non-porous solid surfaces (van Bekkum et al., 1994; Jansen et al., 1994), including the surfaces of dielectric microwave-responsive materials. Coatings of zeolites can be either films or layers. A film is a continuous solid phase of microporous crystals oriented in a parallel mode on a support. A layer is a (dis) continuous solid phase of microporous crystals more or less disorderly oriented on a support. The preparation of zeolite coatings is well known (Jansen et al., 1994). The coatings can be formed by application of the formed zeolites, or by growing the zeolites on the surface.

In this example, Y zeolites (Zeolyst International, Valley Forge, Pa.) are affixed to an approximately 0.5 cm×0.5 cm surface of Bentonite 200 clay by the technique of dip coating. (Alternatively, other dielectric materials such as carbon could be used as the support.) Dip-coating is an efficient and well-proven method to apply zeolites to surfaces and may be used with most support surfaces (van Bekkum et al., 1994). The Y zeolites are made into a slurry containing a dissolved polymeric substance, which forms the continuous phase layer after solvent removal. The binder, which is commonly added, which upon curing assists in the formation of a strongly bonded zeolite layer on the surface.

Example 7

Microwave-Accelerated Homolytic Cleavage of 1-Naphthyl Phenylacetate on a Zeolite Y-Coated Clay Dielectric Surface A Zeolite Y-coated clay chip (Example 6) is placed in the bottom of a 50 mL beaker. Hexane (20 mL) containing 1-naphthyl phenylacetate (NP) (10 mM) is added (Gu et al., 1999). The beaker is placed in a microwave oven (Panasonic NN-S949, 1100 W output, 2.45 GHZ) and microwaves are generated until the reaction occurs on the zeolite surface. Following irradiation, the bulk hexane solution is characterized by gas chromatography as described (Gu et al., 1999). The surface zeolites are extracted into pure hexane and the extract is also characterized by GC. The extent of the reaction of NP is greater in the zeolite extract than in the bulk hexane solution (there is a higher product-to-reactant concentration ratio).

In a second experiment, two zeolite-coated clay chips are immersed in separate beakers containing 10 mM NP in hexane. One beaker is exposed to microwave irradiation, while the other beaker is not. The zeolite-clay chips are extracted into hexane, and analyzed by GC. The microwave-irradiated zeolite will contain a higher product-to-reactant ratio than the non-micro waved zeolite.

Example 8

Coating a Dielectric Molecular Imprinted Polymer with an Insulating Mesoporous Silica Layer In some cases it might be necessary to further encapsulate the dielectric/artificial enzyme composite. A porous thermally insulating capsule or layer would reduce heat transfer from the dielectric to the bulk solvent. (It is also noted above, that an equivalent result could be obtained by cooling the bulk solution using a cooled container.)

A number of materials, primarily polymers, could be used as the insulating layer. The requirements of such materials are that it must reduce heat transfer while also, at least minimally, allowing reactants to pass through. The thickness of the porous layer can be optimized depending on various factors including the reaction to be catalyzed, the types of materials used, and the specific application desired.

In the case of a molecularly imprinted polymer, one technique is to coat the surface of the imprinted polymer with the same polymer, minus the print molecule. Thus, the order of materials would be dielectric/imprinted polymer/non-imprinted polymer/bulk solution. As referenced above, forming layers of polymers is known in the art.

The present example describes how a porous silica layer can be used to coat and insulate an dielectric/artificial enzyme composite. A dielectric surface coated with a layer of molecularly imprinted polymer is coated with silica. To coat an imprinted polymer with a silica layer, a stock solution is first prepared (Makote et al., 1998). The solution contains tetramethoxysilane (TMOS), phenyltrimethoxysilane (PT-MOS), ethoxy ethanol (EE), water, and 0.1 M hydrochloric acid. The ratio of TMOS to PTMOS is 10:1. The pH of the solution is raised to 7 using potassium hydroxide. After 30 minutes, the solution is coated on the dielectric/molecularly-imprinted polymer. The coating method can be by using a spin-coater (Makote et al., 1998), or spraying, or dip coating. The resultant coated surface is allowed to dry in a dessicator at room temperature. To further enhance the insulating properties of the silica coat, the coating process can be repeated multiple times to form multiple layers.

Example 9

Film-Based Detection of Microwave-Accelerated Chemiluminescence

A number of experiments were carried out to test the invention using chemiluminescence reactions. In the experiments, microscope slides were prepared as "chips" on which luminol/peroxide reactions took place to give light. The chips were either plain (glass) or had a dielectric. Dielectrics used were barium titanate or activated charcoal. Film was used to detect light from the CL reactions, with and without microwave irradiation.

Experimental:

Chips: Dielectric chips were made from standard microscope slides (1 inch×3 inch×1 mm) (VWR Micro Slides). Two types of chips were made. One type was made by spotting dielectric slurries onto microscope slides. Spots were approximately 0.5 cm in diameter. The CL reaction was then run directly on top of (in contact with) the dielectric. The other type of chip was a sandwich of two microscope slides with nothing (control chips) or a contiguous film of dielectric between the slides. With the "sandwich chips", the CL reaction was run on the upper glass slide, not in contact with the dielectric layer. The dielectrics used were barium titanate (Aldrich Chemical Co., 20, 810-8) and activated charcoal (Sigma Chem. Co. C4386). Thick slurries of dielectrics were prepared by mixing with water. Barium titanate formed a thick paste and charcoal formed a less dense mixture.

Chemiluminescent Reactions: Luminol (3-aminophthalhydrazide monosodium salt, Alfa Aesar 44007) reacts with hydrogen peroxide at alkaline pH. Solutions of luminol were prepared at various pH values from approximately 7.9-10.2. The solutions also contained copper(II)sulfate pentahydrate and buffer (sodium bicarbonate). Various concentrations and pH values were tried, but it was finally determined to use pH 8.0 and a luminol concentration of luminol was 4.4 mM (stock solution, which was mixed 1:1 with the peroxide solution to initiate the reaction). At higher pH values the reaction went too fast and was apparently more than halfway completed in the first minute. The lower pH caused the reaction to proceed much more slowly. Lower luminol concentrations were feasible but 4.4 mM was desired to obtain bright spots on film.

The luminol solution was mixed with an equal volume of dilute hydrogen peroxide to begin the CL reaction. Hydrogen peroxide, 3%, was diluted 1:20. This was the stock solution (0.15%).

On chips, the total volume of the spots was either 6.0 µL (3.0 of each luminol and peroxide) or 3.0 µL (1.5 of each).

Data Recording: To be most sensitive, the technology will use CCD or PMT detection and analysis of CL light. Alternatively, it is convenient to use film, especially in cases where quantitation is not critical, but a qualitative measure of some signal is needed. Additionally, a film-based system may be attractive where disposables are needed, rather than say, a CCD camera.

Data was recorded on sheets of Amersham Hyper ECL film and developed according to conventional methods. In all cases, under microwave irradiation or not, film was exposed to CL chips for 20 seconds. Film development was through conventional means (Kodak D-19 developer).

Chip Holder: A chip holder was made from a music CD case. The clear methyl methacrylic case acted as a thermal insulator to prevent the film from getting hot. It also prevented the film from contacting the reaction surface. The CD case had within it a cardboard insert to prevent chips from moving. The edges of the film were taped lightly to the outside of the CD box over the chips, and the CD box was placed in a light-tight cardboard box. The box was then placed in a microwave oven (see Example 1 for description of the oven).

Experiments Performed and Results: In all cases, chips were used once and discarded. Microwaving was performed on a rotating tray to reduce uneven heating. No evidence of artifacts due to uneven heating was observed (multiple experiments gave results that were in agreement with each other).

1) Spotted Chips. Initial work with spotted chips gave equivocal results. This is believed due to the fact that the reagents were spotted directly onto the dielectric material. The reactants may have soaked into the dielectric layer somewhat or spread unevenly. It was difficult to determine the success or failure of the experiments using both carbon and barium titanate dielectric layers for this reason. It should be noted that direct contact of the dielectric and the binding reagents is not a requirement of the invention (see FIG. 2).

2) Sandwich Chips. Results with so-called sandwich chips were much better than with spotted chips. As stated above, sandwich chips comprise three layers; a microscope slide, a middle dielectric layer, and another microscope slide. These chips have two major advantages over spotted chips used above. One is that the reaction occurs on glass (a known surface) rather than on an uneven dielectric spot. The second advantage is that the dielectric layer is large, covering the entire 1×3 inch surface of a slide. This larger amount of dielectric means that the chip can be hotter. (It should be noted that the surface of sandwich chips can be partitioned into hot and cold zones by adding additional non-contiguous layers.)

a) In one experiment 3 µL of luminol stock solution was mixed with 3 µL of peroxide stock solution. There were 2 spots on each of three chips, glass (no dielectric), barium titanate, and activated charcoal. The chips were placed side-by-side in a chip holder and film taped to the holder. The chips were microwave-heated for 20 seconds and the film was developed. The developed film revealed that there was some light emitted from the glass chip (two spots could be seen) but much more light emitted from the barium titanate spots and the charcoal spots. Indeed, the charcoal chip gave a huge amount of light that was scattered, suggesting that the heat (20 seconds) was so intense that the reagent spots sprayed. Upon opening the chip holder following microwaving, the chips were all visible intact and the dielectric chips, were dramatically hotter to the touch than the control-chip.

b) In a second experiment, the experiment described in a) was repeated. Essentially the same results were obtained.

c) In a third experiment, three chips were again spotted, this time with 1.5 µL each of luminol and peroxide per assay (half the amount used above). It was observed by eye that luminescence a room temperature glowed steadily for several minutes. For this reason, the chips were first assayed at room temperature (20 seconds exposure to film), then placed in the microwave with new film and exposed for another 20 seconds during microwaving. After developing, the two films were compared. The film exposed to chips (20 sec.) prior to microwaving showed light spots corresponding to the CL reactions on all three ships. (Although all were fairly faint, the barium titanate chips consistently gives darker spots in control experiments, suggesting that the white color of the dielectric reflects light upward to the film.) The film exposed to slides during microwaving looked very different. The glass (no dielectric) chip showed no difference from the room temperature exposure—the spots were light. However, the film captured dramatically more light over the dielectric chips. The barium titanate chip gave darker spots that in the control (room temperature) experiment. As seen previously, the image of the activated charcoal spots was very intense and scattered, suggesting that a very large amount of light was emitted and the temperature may have been very high. This experiment demonstrates, as above, that microwave heating accelerates CL reactions on a dielectric chip.

d) The experiment described in c) was repeated with virtually identical results. The room temperature spots were faint, but the microwave spots (with the exception of the control spots) gave dark images on film. These data clearly demonstrate reduction to practice of microwave targeted accelerated reactions.

e) An experiment was performed to verify that the dark spots seen on film were indeed from the CL reactions and not an artifact of the chips themselves. Four chips were prepared; control (two glass microscope slides), barium titanate, activated charcoal, and another dielectric chip, containing Bentonite clay (prepared from powder with deionized water). No CL reagents were placed on the chips. The four chips were placed in the chip holder, X-ray film was attached and the holder was microwaved for 20 seconds. The developed film was completely blank, indicating that all the darkness on films seen originated from CL light emission.

f) The experiment described in c) and d) was repeated except for two variations. One change was that less activated charcoal was used in the chip. The other change was that four chips instead of three were used—a Bentonite clay dielectric chip was added. FIG. 7 shows the results. Each vertical lane is the image from one microscope slide-based chip. On the film can be seen two faint spots in the Control lane. These represent CL emission from two assay spots on the glass-only chip. The other chips show stronger light emission; barium titanate spots, activated charcoal, and Bentonite clay. All of these substances can be used to accelerate chemical reactions on a chip.

REFERENCES

Below is a list of publications cited in the application:

Dielectric Heating/Materials

Microwave Processing of Materials V. in Mat. Res. Soc. Symp. Proc. 430, (1996) Iskander, M F et al., eds.

ASTM Committee E20 on Temperature Measurement (1993) ASTM, Philadelphia.

Baziard, Y & Gourdenne, A (1988) Eur. Polym. J. 24, 873.

Boon, M. E. & Kok, L. P. (1989) in Microwave Cookbook of Pathology, p. 17, Coulomb Press, Leiden.

Bose, A. K. et al. (1997) CHEMTECH 27(9), 18-25.

Bradley, D. (2001) Modern Drug Discovery 4(8), 32-36.

Bram, G., Loupy, A., Majdoub, M., and Petit, A. (1991) Chem. Ind. 396.

Buffler, C. R. & Risman, P. O. (1996) Mat. Res. Soc. Symp. Proc. 430, 85.

Committee on Microwave Processing of Materials, National Materials Advisory Board, Commission on Engineering and Technical Systems, and National Research Council (1994) Microwave Processing of Materials. Washington, D.C., National Academy Press.

Ewart, T. G. & Gavin, G. T. (1999) Nanoparticles Biosensor, U.S. Pat. No. 5,922,537.

Hasted, J. B. Aqueous Dielectrics (1973) Chapman & Hall, London.
Holworth, A. et al. Ind. Eng. Chem. Res. (1998) 37, 2701.
Huhmer, A. F. R. and Landers, J. P (2000) Anal. Chem. 72, 5507-5512.
Jin, Q. et al. (1999) Trends Anal. Chem. 18, 479-484.
Kidwai, M., Kohli, S., Saxena, R. K., Gupta, R., and Bardoo, S. (1998) Ind. J. Chem. 37B, 963.
Kreider, K. G. (1989) Thin Film Thermocouples For High Temperature Measurement. NIST, Springfield, Va.
Kubrakova, I. V. (2000) J. Anal. Chem. 55, 1113-1122.
Mingos, D M P & Baghurst, D R (1991) Chem. Soc. Rev. 20, 1-47.
Olmedo, L. et al. (1993) Adv. Mater. 5, 373.
Roussy, G. & Pearce, J. A. Foundations and Industrial Applications of Microwave and Radio Frequency Fields. Physical and Chemical Processes. Wiley & Sons (1995) New York.
Schultz, P. G. et al. (1999) U.S. Pat. No. 5,985,356
Schultz, P. G., Xiang, X., & Goldwasser, I. (1999) Combinatorial Synthesis of Novel Materials, U.S. Pat. No. 5,985,356.
Slyanev, M. N. (2001) Anal. Chem. 73, 4037-4044.
Varma, R. (2001) AMPERE Newsletter, Issue 29, ISSN 1361-8598.
Xiang, X. (1998) Biotechnol. Bioeng. 227.
Yang, P. et al. (1998) Science 282, 2244.
Zlotorzynski, A. Crit. Rev. Anal. Chem. (1995) 25, 43.

Molecular Imprinting, Zeolites, and Other Binding Molecules
Borchart, A. & Still, W. C. (1994) J. Am. Chem. Soc. 116, 373.
Breslow, R. et al. (1983) J. Am. Chem. Soc. 105, 2739.
Burow, M. & Minoura, N. (1996) Biochem. Biophys. Res. Commun. 227, 419.
Bystrom, S. E. et al. (1993) 115, 2081.
Dai, S. et al. (1999) Angew. Chem. Int. Ed. 38, 1235.
Dickert, F L & Thierer S (1996) Adv. Mater. 8, 987.
Fleischer, C. T. & Boos, K.-S. (2001) American Laboratory, May, 20-25.
Glad et al. (1985) J. Chromatogr. 347, 11.
Gu, W. et al. (1999) J. Am. Chem. Soc. 121, 9467.
Jansen, J. C. et al. (1994) in Advanced Zeolite Science and Applications, J. C. Jansen et al., eds., pp. 215-250, Elsevier, New York.
Jones, K. D. (2001) IVD Technology 7(6) 50-54.
Kempe et al. (1995) J. Mol. Recog. 8, 35.
Krishnan, T. R. & Ibraham, I. (1994) J. Pharm. Biomed. Anal. 12, 287-294.
Leonhardt, A. & Mosbach, K. (1987) Reactive Polymers 6, 285.
Makote, R. & Collinson, M. M. (1998) Chem. Commun. 3, 425.
Mathew-Krotz, J. & Shea, K. J. (1995) J. Am. Chem. Soc. 118, 8134.
Maugh, T. H. (1984) Science 223, 269.
Maugh, T. H. (1983) Science 221, 351.
Maugh, T. H. (1983) Science 222, 151.
Norrlow, O. et al. (1984) 299, 29.
O'Shannessy et al. (1989a) Anal. Biochem. 177, 144.
O'Shannessy et al. (1989b) J. Chromatogr. (1989b) 470, 391.
Rouhi, A. M. (2000) Chem. Eng. News 78 (34) 40.
Shi et al. (1999) Nature 398, 593.
van Bekkum, H. et al. (1994) in Advanced Zeolite Science and Applications, J. C. Jansen et al., eds., pp. 509-542, Elsevier, New York.

Macroporous Coatings
Jiang, P. et al. (1999) J. Am. Chem. Soc. 121, 11630.
Mokaya, R. (1999) Angew. Chem. Int. Ed. 38, 2930.

Microchips/Microarrays and Assays
Cooper, C. S. (2001) Breast Cancer Res. 3, 158-175.
Lennon, G. G. (2000) Drug Discov. Today 5, 59-66.
Pasinetti, G. M. (2001) J. Neurosci. Res. 65, 471-476.
Draghici, S. et al. (2001) Curr. Opin. Drug Discov. Dev. (2001) 4, 332-337.
Schmalzing, D. et al. (2000) Electrophoresis 21, 3919-3930.
Zubritsky, E. (2001) Modern Drug Discov., May issue, 59-71.
Dolle, R. E. (2000) J. Comb. Chem. 2, 383-433.
Robinson, J. K. (2000) American Laboratory, December, 28-34.

Practical Applications in Biomedicine
Bowie, A. R., Sanders, M. G., & Worsfold, P. J. (1996) J. Biolumin. Chemilumin. 11, 61-90.
Roda, A., Pasini, P., Guardigli, M., Baraldini, M., Musiani, M., & Mirasoli, M. (2000) Fresenius J. Anal. Chem. 366, 752-9.
Wood, W. G. (1984) J. Clin. Chem. Clin. Biochem. 22, 905-918.
Folkman, J. (1997) EXS 79, 1-8.
Saaristo, A., Karpanen, T., and Alitalo, K. (2000) Oncogene 19, 6122-6129.
Sidransky, D. (1997) Science 278, 1054-1058.
Abati, A. & Liotta, L. A. (1996) Cancer. 78, 1-3.
Marx, J. (2000) Science 289, 1670-1672.
Latchman, D. S. (1995) PCR Applications in Pathology. Principles and Practice. NY, Oxford Univ. Press.
Freeman, W. M., Walker, S. J., & Vrana, K. E. (1999) BioTechniques 26, 112-125.
Seiden, M. L. & Sklar, J. L. (1996) in Important Advances In Oncology, D. T. DeVita, ed., Philadelphia, Lippincott-Raven.
Schena, M., Shalon, D., Davis, R. W., & Brown, P. O. (1995) Science 270, 467-470.
Harkin, D. P. (2000) Oncologist 5, 501-7.
Kricka, L. J. (1999) Clin. Chem. 45, 453-8.
Leitzel, K., Lieu, B., Curley, E., Smith, J., Chinchilli, V., Rychlik, W., & Lipton, A. (1998) Clin. Cancer Res. 4, 3037-3043.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for detecting a chemical reaction of a reactant, said method comprising:
    (a) contacting said reactant with a solid composite, said composite comprising a material susceptible to microwave heating and a specific binding molecule for the reactant, said contacting being conducted under conditions sufficient to allow said reactant to bind to said specific binding molecule of said composite via a biospecific interaction, wherein said specific binding molecule is thermally proximal to said solid material to thereby provide the reactant thermally proximal to the solid material upon binding;

(b) applying an electromagnetic field of a wavelength of between 1 cm and 100 m to said composite, resulting in microwave heating of said solid material, wherein said heated solid material heats said thermally proximal reactant, wherein said chemical reaction is accelerated by said heating of said reactant; and (c) detecting a physical or chemical property associated with said chemical reaction.

2. The method of claim 1, wherein said step of contacting comprises mixing said composite into a solution containing said reactant.

3. The method of claim 1, wherein said chemical reaction is hydrolysis, homolytic cleavage, or a chemiluminescent reaction.

4. The method of claim 1, wherein said reactant is capable of producing a physical or chemical property associated with said chemical reaction.

5. The method of claim 4, wherein the physical or chemical property associated with said chemical reaction is color, luminescence, fluorescence or electrochemistry.

6. The method of claim 4, wherein the production of the physical or chemical property is accelerated by said heating of said reactant.

7. The method of claim 1, wherein said step of detecting further comprises detecting a change in the physical or chemical property associated with said chemical reaction.

8. The method of claim 1, wherein said step of detecting comprises the use of x-ray film, a photomultiplier tube (PMT) or a charge-couple device (COD) camera.

9. The method of claim 1, wherein said solid material is selected from the group consisting of carbon, charcoal, amorphous carbon, carbon black, clay, and nickel.

10. The method of claim 1, wherein said solid material is an oxide selected from the group consisting of copper oxide, chromium oxide, silicon oxide, niobate oxide and manganese oxide.

11. The method of claim 1, wherein said solid material is a titanate selected from the group consisting of barium titanate, and an inorganic titanate.

12. The method of claim 1, wherein said solid material is an oxide or non-oxide ceramic, a ferrite, a ferroelectric polymer, or an organic polymer.

13. The method of claim 1, wherein said solid material is selected from the group consisting of SiC, Si, Mg, FeSi, $Cr_2O_3$, $Fe_3O_4$, $MnO_2$, NiO.

14. The method of claim 1, wherein said solid material is a mixture of a conductive material and an insulator.

15. The method of claim 1, wherein said specific binding molecule is selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

16. The method of claim 1, wherein said reactant is selected from the group consisting of an antigen, receptor ligand, enzyme inhibitor, enzyme substrate, enzyme product, and oligonucleotide.

17. The method of claim 1, wherein said reactant is a covalent conjugate of a small molecule and a molecule selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

18. The method of claim 1, wherein said specific binding molecule has at least one binding site for said reactant, said binding site facilitating more than one reaction turnover.

19. The method of claim 1, wherein said specific binding molecule has at least one binding site for said reactant, said binding site facilitating one reaction turnover.

20. The method of claim 1, wherein said electromagnetic field is applied at a frequency of from about 0.9 to about 25 GHz.

21. The method of claim 20, wherein said electromagnetic field is applied at a frequency of from about 0.9 to about 6 GHz.

22. The method of claim 21, wherein said electromagnetic field is applied at a frequency of from about 0.9 to about 2.5 GHz.

23. The method of claim 20, wherein said electromagnetic field is applied at a frequency selected from the group consisting of 0.915, 2.45, 5.85 and 22.125 GHz.

24. The method of claim 1, in which said composite is in the form of a planar substrate.

25. The method of claim 1, wherein said solid material susceptible to microwave heating comprises a dielectric material, and wherein said application of said electromagnetic field additionally results in dielectric heating.

26. The method of claim 1, wherein said solid material is more susceptible to microwave heating than water.

27. A method for detecting a chemical reaction of a reactant, said method comprising:

(a) contacting a reactant-containing solution with a solid composite, said composite comprising a specific binding molecule for the reactant and a material susceptible to microwave heating, said contacting being under conditions sufficient to allow said reactant to bind to said specific binding molecule of said composite via a biospecific interaction, thereby forming a composite-reactant complex, wherein said composite-reactant complex is thermally proximal to said solid material;

(b) separating said composite-reactant complex from the solution;

(c) applying an electromagnetic field of a wavelength of between 1 cm and 100 m to said composite of said composite-reactant complex, resulting in microwave heating of the solid material of said complex,—whereby said heated solid material heats said reactant of said thermally proximal composite—reactant complex, wherein said chemical reaction is accelerated by said heating of said reactant of said composite-reactant complex; and (d) detecting a physical or chemical property associated with said chemical reaction.

28. The method of claim 27, wherein said chemical reaction is hydrolysis, homolytic cleavage, or a chemiluminescent reaction.

29. The method of claim 27, wherein said reactant is capable of producing a physical or chemical property associated with said chemical reaction.

30. The method of claim 27, wherein the physical or chemical property associated with said chemical reaction is color, luminescence, fluorescence or electrochemistry.

31. The method of claim 27, wherein the production of the physical or chemical property is accelerated by said heating of said reactant.

32. The method of claim 27, wherein said step of detecting further comprises detecting a change in the physical or chemical property associated with said chemical reaction.

33. The method of claim 27, wherein said step of detecting comprises the use of x-ray film, a photomultiplier tube (PMT) or a charge-couple device (COD) camera.

34. The method of claim 27, wherein said solid material is selected from the group consisting of carbon, charcoal, amorphous carbon, carbon black, clay, and nickel.

35. The method of claim 27, wherein said solid material is an oxide selected from the group consisting of copper oxide, chromium oxide, silicon oxide, niobate oxide and manganese oxide.

36. The method of claim 27, wherein said solid material is a titanate selected from the group consisting of barium titanate, and an inorganic titanate.

37. The method of claim 27, wherein said solid material is an oxide or non-oxide ceramic, a ferrite, a ferroelectric polymer, or an organic polymer.

38. The method of claim 27, wherein said solid material is selected from the group consisting of SiC, Si, Mg, FeSi, $Cr_2O_3$, $Fe_3O_4$, $MnO_2$, NiO.

39. The method of claim 27, wherein said solid material is a mixture of a conductive material and an insulator.

40. The method of claim 27, wherein said specific binding molecule is selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

41. The method of claim 27, wherein said reactant is selected from the group consisting of an antigen, receptor ligand, enzyme inhibitor, enzyme substrate, enzyme product, and oligonucleotide.

42. The method of claim 27, wherein said reactant is a covalent conjugate of a small molecule and a molecule selected from the group consisting of a molecularly imprinted polymer, a zeolite, an antibody, a modified antibody, an enzyme, a modified enzyme, a cavitand, a chiral ligand, a low molecular weight organic synthetic receptor, single stranded nucleic acid, and double stranded nucleic acid.

43. The method of claim 27, wherein said specific binding molecule has at least one binding site for said reactant, said binding site facilitating more than one reaction turnover.

44. The method of claim 27, wherein said specific binding molecule has at least one binding site for said reactant, said binding site facilitating one reaction turnover.

45. The method of claim 27, wherein said electromagnetic field is applied at a frequency of from about 0.9 to about 25 GHz.

46. The method of claim 45, wherein said electromagnetic field is applied at a frequency of from about 0.9 to about 6 GHz.

47. The method of claim 46, wherein said electromagnetic field is applied at a frequency of from about 0.9 to about 2.5 GHz.

48. The method of claim 45, wherein said electromagnetic field is applied at a frequency selected from the group consisting of 0.915, 2.45, 5.85 and 22.125 GHz.

49. The method of claim 27, in which said composite is in the form of a planar substrate.

50. The method of claim 27, wherein said solid material susceptible to microwave heating comprises a dielectric material, and wherein said application of said electromagnetic field additionally results in dielectric heating.

51. The method of claim 27, wherein said solid material is more susceptible to microwave heating than water.

* * * * *